(12) United States Patent
Erramilli et al.

(10) Patent No.: US 12,205,693 B2
(45) Date of Patent: Jan. 21, 2025

(54) PHARMACEUTICAL CONTENT GENERATION BASED ON USER TYPE

(71) Applicant: ACTO Technologies Inc., Toronto (CA)

(72) Inventors: Kumar Karthik Erramilli, Pickering (CA); Parth Khanna, Toronto (CA); Kapil Kalra, Mississauga (CA)

(73) Assignee: ACTO Technologies Inc., Toronto (CA)

( * ) Notice: Subject to any disclaimer, the term of this patent is extended or adjusted under 35 U.S.C. 154(b) by 852 days.

(21) Appl. No.: 17/170,067

(22) Filed: Feb. 8, 2021

(65) Prior Publication Data

US 2022/0254463 A1 Aug. 11, 2022

(51) Int. Cl.
| | |
|---|---|
| *G16H 15/00* | (2018.01) |
| *G06F 40/174* | (2020.01) |
| *G06F 40/186* | (2020.01) |
| *G06Q 10/10* | (2023.01) |
| *G16H 20/10* | (2018.01) |
| *G16H 40/20* | (2018.01) |

(Continued)

(52) U.S. Cl.
CPC ........... *G16H 15/00* (2018.01); *G06F 40/174* (2020.01); *G06F 40/186* (2020.01); *G16H 20/10* (2018.01); *G16H 40/20* (2018.01); *G16H 50/70* (2018.01); *G16H 70/40* (2018.01); *G06Q 10/10* (2013.01)

(58) Field of Classification Search
CPC ........ G16H 15/00; G16H 20/10; G16H 40/20; G16H 50/70; G16H 70/40; G16H 10/20; G06F 40/174; G06F 40/186; G06F 40/103; G06Q 10/10

USPC ........................................................ 705/2-3
See application file for complete search history.

(56) References Cited

U.S. PATENT DOCUMENTS

| | | | |
|---|---|---|---|
| 10,991,009 B2 * | 4/2021 | Marsh ................ | G06Q 30/0269 |
| 2013/0262196 A1 * | 10/2013 | Scalici ................. | G16H 70/40 |
| | | | 705/14.1 |

(Continued)

FOREIGN PATENT DOCUMENTS

WO WO-2021137238 A1 * 7/2021 ............. G16H 10/60

*Primary Examiner* — Joy Chng
(74) *Attorney, Agent, or Firm* — Fernando & Partners, LLP

(57) ABSTRACT

Various implementations disclosed herein include devices, systems, and methods for tailoring information regarding a pharmaceutical article to user types. In various implementations, a device includes a non-transitory memory and a processor coupled with the non-transitory memory. In some implementations, a method includes obtaining a request to synthesize a plurality of pharmaceutical content items for respective user types. In some implementations, the plurality of pharmaceutical content items provides information regarding a pharmaceutical article. In some implementations, the method includes determining, for the respective user types, corresponding expected engagement values indicative of expected engagement with the subject. In some implementations, the method includes determining, based on the corresponding expected engagement values, respective content templates for the plurality of pharmaceutical content items. In some implementations, the method incudes synthesizing the plurality of pharmaceutical content items by populating the respective content templates with information regarding the pharmaceutical article.

20 Claims, 11 Drawing Sheets

(51) Int. Cl.
*G16H 50/70* (2018.01)
*G16H 70/40* (2018.01)

(56) References Cited

U.S. PATENT DOCUMENTS

2018/0276184 A1* 9/2018 Krishna ................ G06F 16/986
2020/0226164 A1* 7/2020 Eifert .................. G06F 16/3334

* cited by examiner

PHARMACEUTICAL CONTENT GENERATION BASED ON USER TYPE

TECHNICAL FIELD

The present disclosure generally relates to pharmaceutical content generation based on user type.

BACKGROUND

Some devices allow users to generate content. For example, some devices allow users to generate textual content and publish the textual content. Similarly, some devices allow users to record videos that the users can upload to a content distribution platform. Generating content for various audiences is resource-intensive.

BRIEF DESCRIPTION OF THE DRAWINGS

So that the present disclosure can be understood by those of ordinary skill in the art, a more detailed description may be had by reference to aspects of some illustrative implementations, some of which are shown in the accompanying drawings.

Figure 1A:
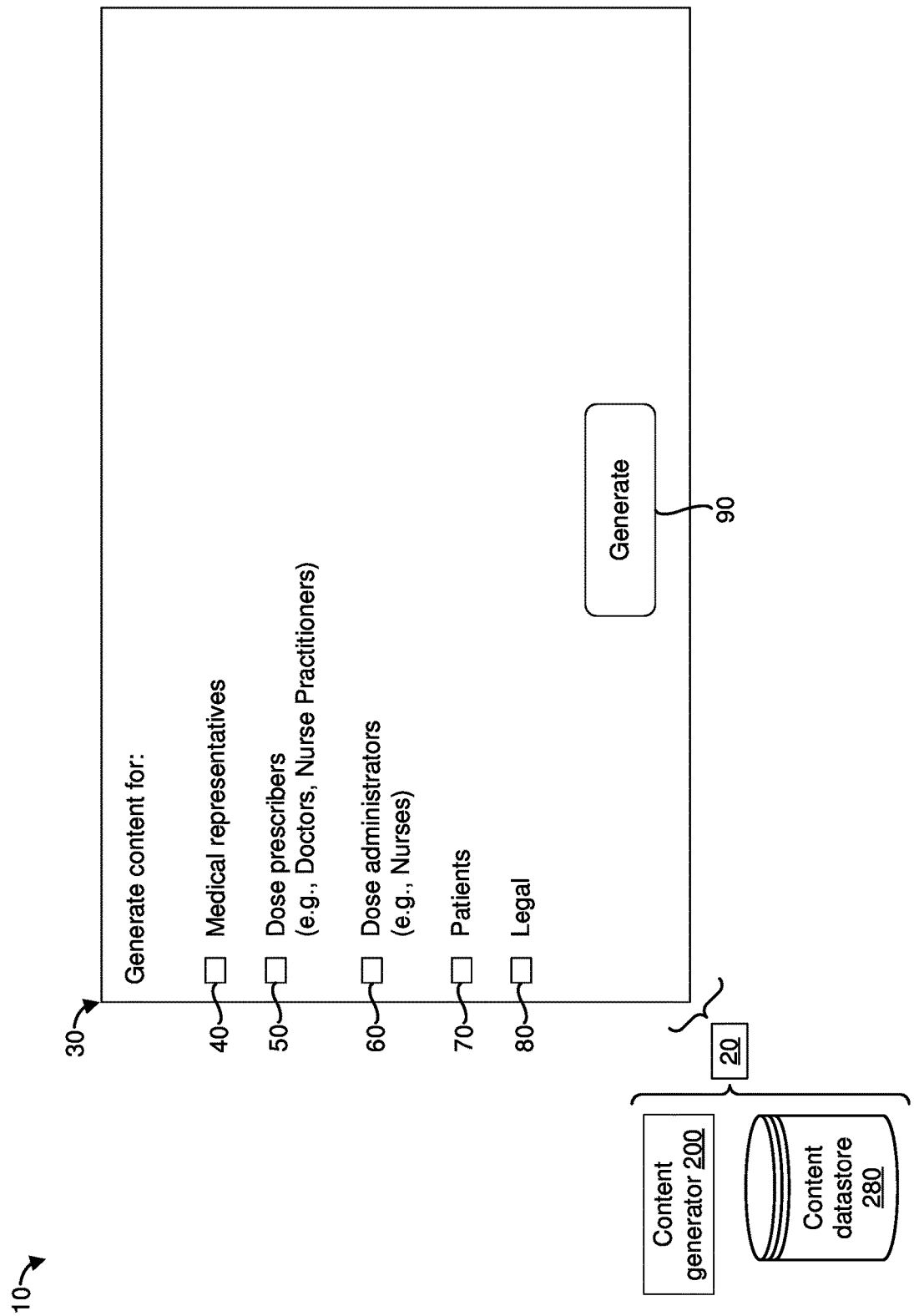
FIGS. 1A-1G are diagrams of an example operating environment in accordance with some implementations.

In accordance with common practice the various features illustrated in the drawings may not be drawn to scale. Accordingly, the dimensions of the various features may be arbitrarily expanded or reduced for clarity. In addition, some of the drawings may not depict all of the components of a given system, method or device. Finally, like reference numerals may be used to denote like features throughout the specification and figures.

SUMMARY

Various implementations disclosed herein include devices, systems, and methods for synthesizing pharmaceutical content items regarding a pharmaceutical article for different user types. In various implementations, a device includes a non-transitory memory and a processor coupled with the non-transitory memory. In some implementations, a method includes obtaining a request to synthesize a plurality of pharmaceutical content items for respective user types. In some implementations, the plurality of pharmaceutical content items provides information regarding a pharmaceutical article. In some implementations, the method includes determining, for the respective user types, corresponding expected engagement values indicative of expected engagement with the pharmaceutical article. In some implementations, the method includes determining, based on the corresponding expected engagement values, respective content templates for the plurality of pharmaceutical content items. In some implementations, the method incudes synthesizing the plurality of pharmaceutical content items by populating the respective content templates with information regarding the pharmaceutical article.

In accordance with some implementations, a device includes one or more processors, a non-transitory memory, and one or more programs. In some implementations, the one or more programs are stored in the non-transitory memory and are executed by the one or more processors. In some implementations, the one or more programs include instructions for performing or causing performance of any of the methods described herein. In accordance with some implementations, a non-transitory computer readable storage medium has stored therein instructions that, when executed by one or more processors of a device, cause the device to perform or cause performance of any of the methods described herein. In accordance with some implementations, a device includes one or more processors, a non-transitory memory, and means for performing or causing performance of any of the methods described herein.

DESCRIPTION

Numerous details are described in order to provide a thorough understanding of the example implementations shown in the drawings. However, the drawings merely show some example aspects of the present disclosure and are therefore not to be considered limiting. Those of ordinary skill in the art will appreciate that other effective aspects and/or variants do not include all of the specific details described herein. Moreover, well-known systems, methods, components, devices, and circuits have not been described in exhaustive detail so as not to obscure more pertinent aspects of the example implementations described herein.

Generating different media content items regarding a subject (e.g., a pharmaceutical article, for example, a pharmaceutical drug or a medical device) for different types of users is resource-intensive because different types of users require different information regarding the subject. Additionally, different presentation styles may be suitable for different types of users. For example, for patients, a short video regarding a pharmaceutical drug may be more suitable than a long clinical study. However, for clinicians that prescribe pharmaceutical drugs, the long clinical study may be more suitable that the short video.

The present disclosure provides methods, systems and/or devices for tailoring information regarding a subject for different types of users by synthesizing different media content items for different user types. The device generates content items for different user types based on content templates associated with the user types. For example, the device generates a first media content item for patients by populating a patient content template with information regarding a pharmaceutical article, a second media content item for healthcare providers by populating a healthcare provider content template with information regarding the pharmaceutical article, and a third media content item for insurance companies by populating an insurance content template with information regarding the pharmaceutical article.

The templates can specify types of information that is to be included in the corresponding media content items. For example, a healthcare provider template can specify that the healthcare provider template is to be populated with information regarding a pharmaceutical drug that healthcare providers may find useful when deciding whether to prescribe the pharmaceutical drug. As an example, the healthcare provider template may include a display element (e.g., a GUI element, for example, an empty text box) that the device can populate with information that provides a comparison of the pharmaceutical drug with another comparable pharmaceutical drug so that healthcare providers can use the comparison to decide whether to prescribe the pharmaceutical drug or the comparable pharmaceutical drug. While the healthcare provider template may include the display element for comparative information, a template for a medical claims processing entity (e.g., an insurance company) may not include the display element for comparative information because the medical claims processing entity does not need to know how the pharmaceutical drug performs relative to other comparable pharmaceutical drugs in order to process a medical claim. As another example, the healthcare provider template may include a display element (e.g., a section) for a journal excerpt but a patient template may not include the display element for the journal excerpt because patients may not be expected to read journal excerpts regarding pharmaceutical drugs.

The templates can specify amounts of information that is to be included in the corresponding media content items. The amounts may be a function of time durations that the user types are expected to engage with information regarding the subject. For example, an amount of information that can be included in a patient template may be less than an amount of information that can be included in a healthcare provider template because patients may be expected to view information regarding a pharmaceutical drug for a shorter time duration than the healthcare providers.

The templates can specify presentation characteristics that define how information regarding the subject is presented to the different user types. The presentation characteristics can include linguistic characteristics. As an example, the patient template may specify that persuasive adjectives can be used in a media content item that is directed to patients. However, a healthcare provider template may specify that persuasive adjectives may not be used in a media content item for healthcare providers because the media content item for healthcare providers is to provide facts in an objective manner rather than a persuasive manner. The templates may be associated with different vocabularies. For example, the healthcare provider template for healthcare providers may direct the device to include pharmacological terms in the media content item for healthcare providers. However, the patient template for patients may direct the device to forgo including pharmacological terms in the media content item for patients or to substitute pharmacological terms with simpler plain English terms so that patients can more easily understand the information being conveyed.

Synthesizing media content items based on expected engagement values increases a relevance of the media content items to the respective user types. Generating media content items that are relevant to specific user types tends to increase engagement with the media content items. Presenting media content items that the users are more likely to engage with tends to reduce an amount of time during which content is displayed without being engaged with thereby reducing unnecessarily keeping a display on. Synthesizing media content items based on expected engagement values tends to conserve computing resources by forgoing generation of content that users may not engage with. For example, foregoing including clinical studies in a media content item for patients tends to reduce power consumption associated with inserting information associated with the clinical studies in the media content item. Forgoing inclusion of information that a user is not expected to engage with tends to reduce power consumption associated with keeping a display on while information that the user does not view is unnecessarily displayed on the display. Conserving computing resources tends to reduce power consumption, and reducing power consumption increases a battery life of a battery-operated device.

FIG. 1A is a diagram of an example operating environment 10 in accordance with some implementations. While pertinent features are shown, those of ordinary skill in the art will appreciate from the present disclosure that various other features have not been illustrated for the sake of brevity and so as not to obscure more pertinent aspects of the example implementations disclosed herein. To that end, as a non-limiting example, the operating environment 10 includes an electronic device 20 ("device 20", hereinafter for the sake of brevity), a content generator 200 and a content datastore 280. As shown in FIG. 1A, in some implementations, the device 20 implements the content generator 200. Although the content generator 200 is shown as being integrated into the device 20, in some implementations, the content generator 200 is separate from the device 20. For example, in some implementations, the content generator 200 is implemented by another device (e.g., a remote device, for example, a server). As shown in FIG. 1A, in some implementations, the device 20 includes the content datastore 280. However, in some implementations, the content datastore 280 is separate from the device 20. For example, in some implementations, the content datastore 280 resides at another device (e.g., a remote device, for example, a server).

In some implementations, the device 20 includes a handheld computing device that can be held by a user (now shown). For example, in some implementations, the device 20 includes a smartphone, a tablet, a media player, a laptop, or the like. In some implementations, the device 20 includes a wearable computing device that can be worn by the user. For example, in some implementations, the device 20 includes an electronic watch or a pair of headphones.

In some implementations, the device 20 displays a content generation graphical user interface (GUI) 30 that allows a user of the device 20 to generate media content items that provide information regarding a subject. The content generation GUI 30 allows the user of the device 20 to specify which user types to generate media content items for. As shown in FIG. 1A, in some implementations, the content generation GUI 30 includes a first affordance 40 corresponding to medical representatives, a second affordance 50 corresponding to healthcare providers that prescribe medications (e.g., dose prescribers such as doctors and/or nurse practitioners), a third affordance 60 corresponding to healthcare providers that administer dosages of medications (e.g., dose administrators such as nurses), a fourth affordance 70 corresponding to patients and a fifth affordance 80 corresponding to legal persons. In some implementations, the affordances 40, 50, 60, 70 and 80 include check boxes that the user of the device 20 can select to check or uncheck. The content generation GUI 30 also includes a generate affordance 90 (e.g., a submit button).

FIG. 1A illustrates a non-exhaustive list of user types. Other user types are also contemplated. For example, in some implementations, the medical representatives may be further categorized into novice medical representatives and expert medical representatives. As an example, a first user type may include novice medical representatives and a second user type may include expert medical representatives. In some implementations, the medical representatives may be further categorized based on a number of years of experience, an amount of knowledge, a number of interactions with healthcare providers, etc. As an example, a first user type may include medical representatives with 0-5 years of experience representing pharmaceutical articles, a second user type may include medical representatives with 5-10 years of experience, a third user type may include medical representatives with 10-20 years of experience, and fourth user type may include medical representatives with more than 20 years of experience.

Figure 1B:
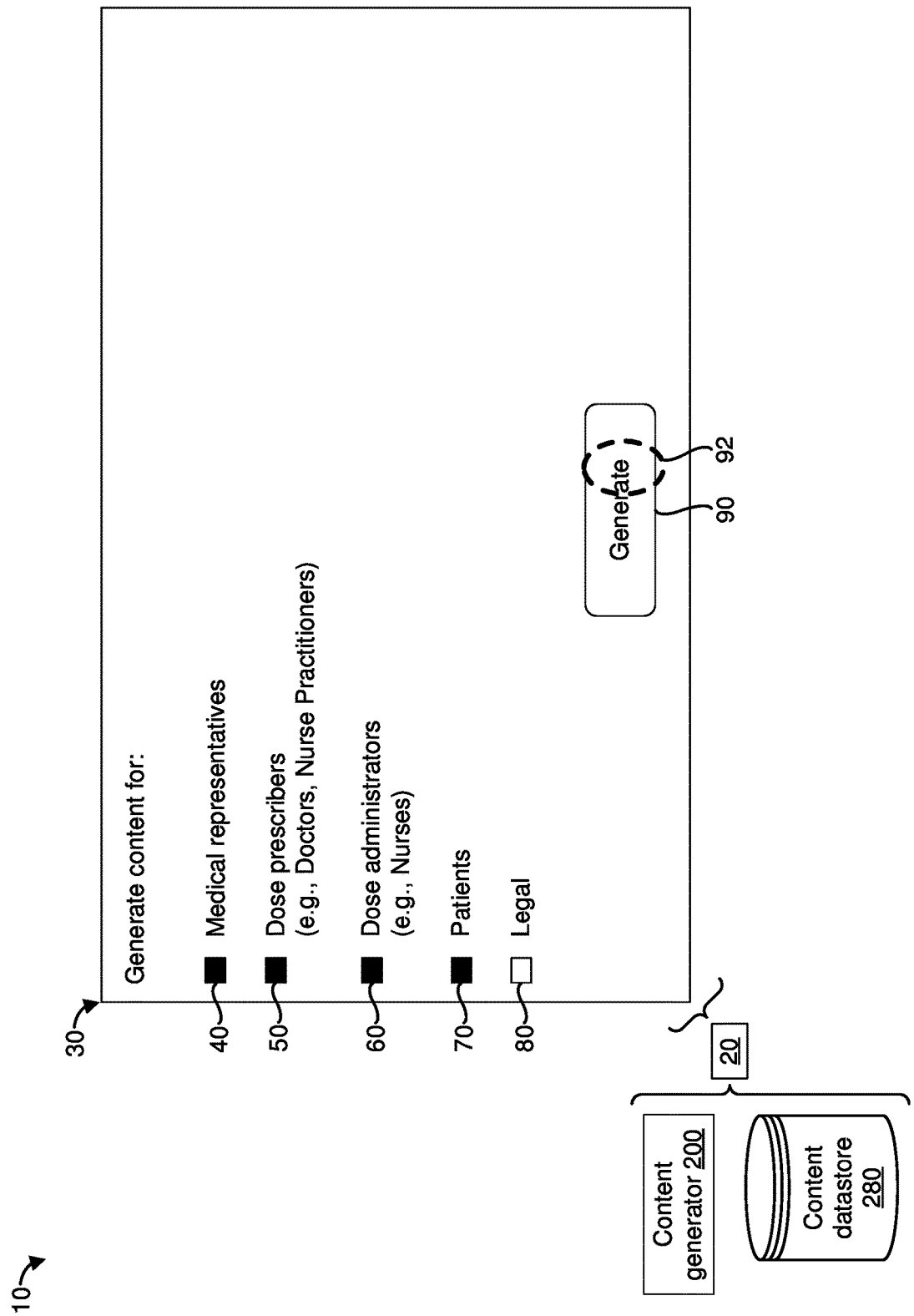

Referring to FIG. 1B, the user has selected the first affordance 40 corresponding to medical representatives, the second affordance 50 corresponding to dose prescribers, the third affordance 60 corresponding to dose administrators and the fourth affordance 70 corresponding to patients. In some implementations, the device 20 detects user inputs (e.g., tap inputs) at locations corresponding to the affordances 40, 50, 60 and 70. As shown in FIG. 1B, the device 20 detects a user input 92 at a location corresponding to the generate affordance 90. In some implementations, the user input 92 corresponds to a request to generate respective media content items for medical representatives, dose prescribers, dose administrators and patients. Since the fifth affordance 80 has not been selected, the device 20 does not generate a media content item for legal persons.

Figure 1C:
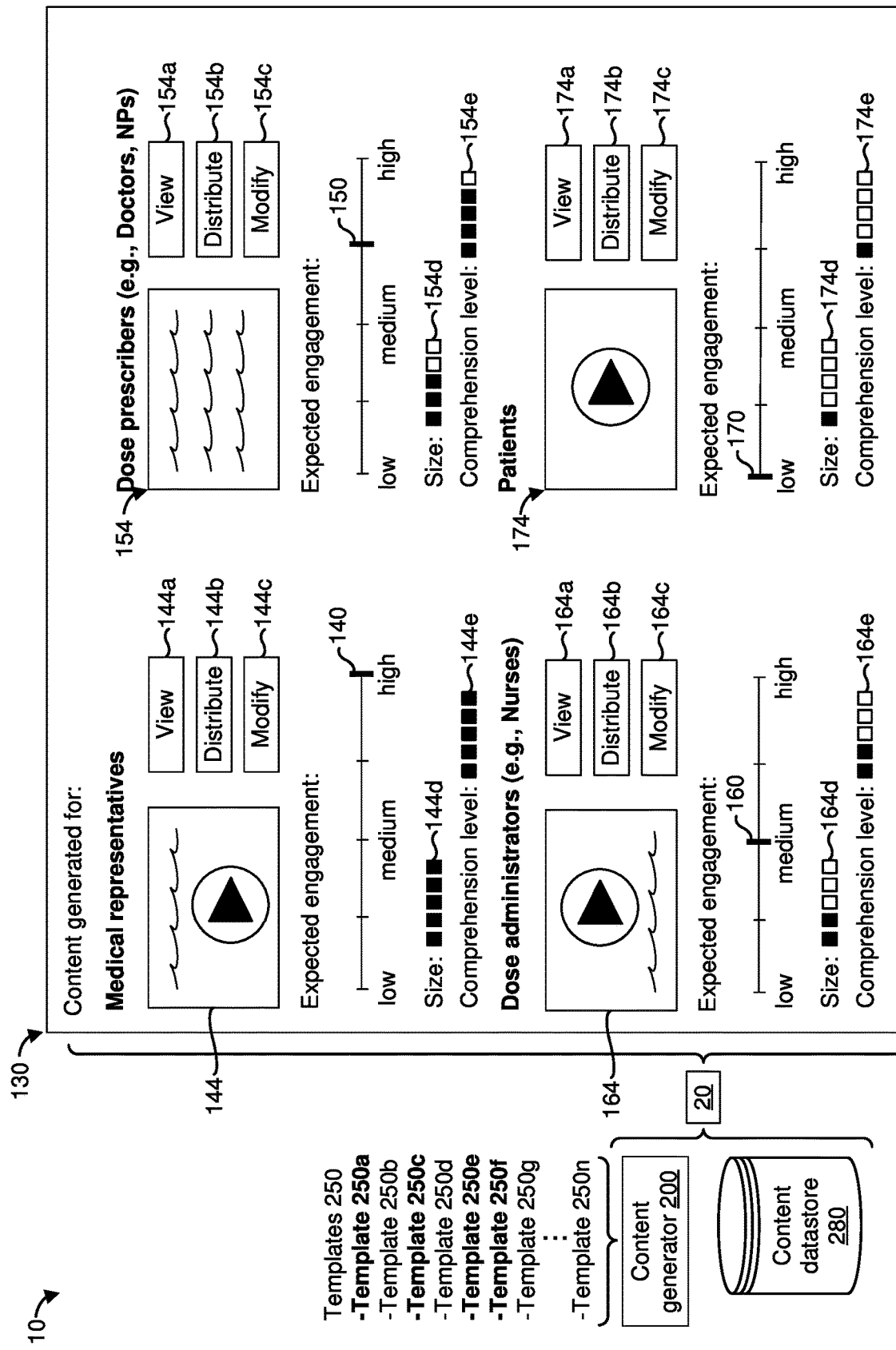

Referring to FIG. 1C, the device 20 displays a content presentation GUI 130 that displays representations of media content items for the medical representatives, the dose prescribers, the dose administrators and the patients. In various implementations, for each user type that was selected in the content generation GUI 30, the device 20 determines a corresponding expected engagement value indicative of expected engagement with the subject (e.g., with information regarding a pharmaceutical drug or a medical device). For example, in some implementations, the device 20 determines a first expected engagement value 140 that indicates an expected engagement of the medical representatives with information regarding a pharmaceutical article (e.g., a pharmaceutical drug or a medical device). In the example of FIG. 1C, the expected engagement of medical representatives with information regarding the pharmaceutical article is 'high'. Similarly, the device 20 determines a second expected engagement value 150 that indicates an expected engagement of the dose prescribers with information regarding the pharmaceutical article. In the example of FIG. 1C, the expected engagement of dose prescribers is between 'medium' and 'high'. The device 20 determines a third expected engagement value 160 that indicates an expected engagement of the dose administrators with information regarding the pharmaceutical article. In the example of FIG. 1C, the expected engagement of the dose administrators is medium. The device 20 determines a fourth expected engagement value 170 that indicates an expected engagement of the patients with information regarding the pharmaceutical article. In the example of FIG. 1C, the expected engagement of the patients is 'low'. As can be seen in FIG. 1C, in some implementations, the expected engagement values 140, 150, 160 and 170 are different from each other.

In various implementations, the expected engagement values 140, 150, 160 and 170 indicate respective amounts of time that the corresponding user types are expected to spend viewing information regarding the subject. For example, in some implementations, the first expected engagement value 140 indicates that the medical representatives are expected to view information regarding a pharmaceutical article for a first amount of time (e.g., over the course of several days). Similarly, in some implementations, the second expected engagement value 150 indicates that the dose prescribers are expected to view information regarding the pharmaceutical article for a second amount of time (e.g., for several hours). In some implementations, the third expected engagement value 160 indicates that the dose administrators are expected to view information regarding the pharmaceutical article for a third amount of time (e.g., for tens of minutes). In some implementations, the fourth expected engagement value 170 indicates that the patients are expected to view information regarding the pharmaceutical article for a fourth amount of time (e.g., for several minutes). As can be seen in FIG. 1C, in some implementations, different user types are expected to spend different amounts of time viewing information regarding the same subject. In the example of FIG. 1C, medical representatives are expected to spend the most amount of time viewing information regarding the pharmaceutical article while patients are expected to spend the least amount of time viewing information regarding the same pharmaceutical article.

In various implementations, the expected engagement values 140, 150, 160 and 170 indicate respective levels of detail that the corresponding user types are expected to be interested in regarding the subject. For example, in some implementations, the first expected engagement value 140 indicates that the medical representatives are likely interested in a first level of detail regarding a pharmaceutical article. Similarly, in some implementations, the second expected engagement value 150 indicates that the dose prescribers are likely interested in a second level of detail that is less than the first level of detail. In some implementations, the third expected engagement value 160 indicates that the dose administrators are likely interested in a third level of detail that is less than the first and second levels of detail. In some implementations, the fourth expected engagement value 170 indicates that the patients are likely interested in a fourth level of detail that is less than the first, second and third levels of detail. As can be seen in FIG. 1C, in some implementations, different user types are expected to be interested in different levels of detail. In the example of FIG. 1C, medical representatives are expected to be interested in the greatest number of details regarding a pharmaceutical article while patients are expected to be interested in the least number of details regarding the same pharmaceutical article.

In various implementations, the content presentation GUI 130 displays representations of media content items that the content generator 200 generated for the various user types. In the example of FIG. 1C, the content presentation GUI 130 includes a representation 144 of a first media content item ("first media content item 144", hereinafter for the sake of brevity) that the content generator 200 generated for medical representatives. The content presentation GUI 130 includes a representation 154 of a second media content item ("second media content item 154", hereinafter for the sake of brevity) that the content generator 200 generated for dose prescribing healthcare providers. The content presentation GUI 130 includes a representation 164 of a third media content item ("third media content item 164", hereinafter for the sake of brevity) that the content generator 200 generated for dose administrating healthcare providers. The content presentation GUI 130 includes a representation 174 of a fourth media content item ("fourth media content item 174", hereinafter for the sake of brevity) that the content generator 200 generated for patients.

In various implementations, the content generator 200 generates the media content items 144, 154, 164 and 174 based on the expected engagement values 140, 150, 160 and 170, respectively. In some implementations, the content generator 200 uses a set of one or more content templates 250 ("templates 250", hereinafter for the sake of brevity) to generate the media content items 144, 154, 164 and 174. As shown in FIG. 1C, the templates 250 include a first template 250*a*, a second template 250*b*, a third template 250*c*, a fourth template 250*d*, a fifth template 250*e*, a sixth template 250*f*, a seventh template 250*g*, . . . , and an nth template 250*n*.

In the example of FIG. 1C, the content generator 200 uses the first template 250*a* to generate the first media content item 144, the third template 250*c* to generate the second media content item 154, the fifth template 250*e* to generate the third media content item 164, and the sixth template 250*f* to generate the fourth media content item 174. In some implementations, the content generator 200 selects the templates 250*a*, 250*c*, 250*e* and 250*f* based on the expected engagement values 140, 150, 160 and 170, respectively. In some implementations, the content generator 200 generates the media content items 144, 154, 164 and 174 by populating the templates 250*a*, 250*c*, 250*e* and 250*f*, respectively, with content stored in the content datastore 280.

In some implementations, the content presentation GUI 130 includes affordances for viewing, distributing and/or modifying the media content items 144, 154, 164 and 174. For example, the content presentation GUI 130 includes a first view affordance 144*a* for viewing the first media content item 144, a first distribute affordance 144*b* for distributing the first media content item 144 to devices associated with medical representatives, and a first modify affordance 144*c* for modifying the first media content item 144. In some implementations, in response to detecting a user input at a location corresponding to the first view affordance 144*a*, the device 20 presents the first media content item 144 on a display of the device 20. In some implementations, in response to detecting a user input at a location corresponding to the first distribute affordance 144*b*, the device 20 triggers transmission of the first media content item 144 to devices associated with medical representatives. For example, in some implementations, the device 20 transmits the first media content item 144 to devices that the medical representatives use in response to detecting an activation of the distribute affordance 144*b*. In some implementations, the device 20 uploads the first media content item 144 to a datastore (e.g., the content datastore 280) that is accessible to the devices of the medical representatives via an application. In some implementations, in response to detecting a user input at a location corresponding to the first modify affordance 144*c*, the device 20 allows a user of the device 20 to modify (e.g., edit) the first media content item 144. For example, in some implementations, the device 20 presents a content modification GUI that allows a user of the device 20 to insert additional content into the first media content item 144 and/or remove existing content from the first media content item 144.

Similar to the affordances 144*a*, 144*b* and 144*c*, in some implementations, the content presentation GUI 130 includes a second view affordance 154*a* for viewing the second media content item 154, a second distribute affordance 154*b* for distributing the second media content item 154 to devices associated with dose prescribers (e.g., to healthcare providers that write prescriptions for medications, for example, to doctors, nurse practitioners and physician assistants), and a second modify affordance 154*c* for modifying the second media content item 154. The content presentation GUI 130 includes a third view affordance 164*a* for viewing the third media content item 164, a third distribute affordance 164*b* for distributing the third media content item 164 to devices associated with dose administrators (e.g., to healthcare providers that administer medications or setup medical devices, for example, nurses), and a third modify affordance 164*c* for modifying the third media content item 164. The content presentation GUI 130 includes a fourth view affordance 174*a* for viewing the fourth media content item 174, a fourth distribute affordance 174*b* for distributing the fourth media content item 174 to devices associated with patients, and a fourth modify affordance 174*c* for modifying the fourth media content item 174.

In some implementations, the content presentation GUI 130 displays a set of one or more characteristic values associated with the media content items 144, 154, 164 and 174. In some implementations, the characteristic values for the media content items 144, 154, 164 and 174 include metadata (e.g., size, file type, etc.) for the media content items 144, 154, 164 and 174. In the example of FIG. 1C, the content presentation GUI 130 includes a first size indicator 144*d* indicating a first size value for the first media content item 144, a second size indicator 154*d* indicating a second size value for the second media content item 154, a third size indicator 164*d* indicating a third size value for the third media content item 164, and a fourth size indicator 174*d* indicating a fourth size value for the fourth media content item 174.

In various implementations, the size values of the media content items 144, 154, 164 and 174 are a function of (e.g., based on) the expected engagement values 140, 150, 160 and 170, respectively. In some implementations, the size values of the media content items 144, 154, 164 and 174 are directly proportional to their corresponding expected engagement values 140, 150, 160 and 170, respectively. For example, the first size value indicated by the first size indicator 144*d* is greater than the fourth size value indicated by the fourth size indicator 174*d* because the first expected engagement value 140 is greater than the fourth expected engagement value 170.

In some implementations, the content presentation GUI 130 indicates respective comprehension levels associated with the media content items 144, 154, 164 and 174. In the example of FIG. 1C, the content presentation GUI 130 includes a first comprehension level indicator 144*e* indicating that the first media content item 144 is associated with a first comprehension level, a second comprehension level indicator 154*e* indicating that the second media content item 154 is associated with a second comprehension level, a third comprehension level indicator 164*e* indicating that the third media content item 164 is associated with a third comprehension level, and a fourth comprehension level indicator 174*e* indicating that the fourth media content item 174 is associated with a fourth comprehension level.

In some implementations, the comprehension levels associated with the media content items 144, 154, 164 and 174 are indicative of respective amounts of cognitive effort required to comprehend the media content items 144, 154, 164 and 174. In some implementations, the comprehension levels associated with the media content items 144, 154, 164 and 174 are indicative of respective amounts of time required to view and understand the information included in the media content items 144, 154, 164 and 174. In some implementations, the comprehension levels associated with the media content items 144, 154, 164 and 174 are indicative of respective levels of required expertise in a domain that the media content items 144, 154, 164 and 174 relate to in order to understand the information included in the media content items 144, 154, 164 and 174.

In various implementations, the comprehension levels associated with the media content items 144, 154, 164 and 174 are a function of (e.g., based on) the expected engagement values 140, 150, 160 and 170, respectively. In some implementations, the comprehension levels associated with the media content items 144, 154, 164 and 174 are directly proportional to their corresponding expected engagement values 140, 150, 160 and 170, respectively. For example, the first comprehension level indicated by the first comprehension level indicator 144e is greater than the fourth comprehension level indicated by the fourth comprehension level indicator 174e because the first expected engagement value 140 is greater than the fourth expected engagement value 170.

Figure 1D:
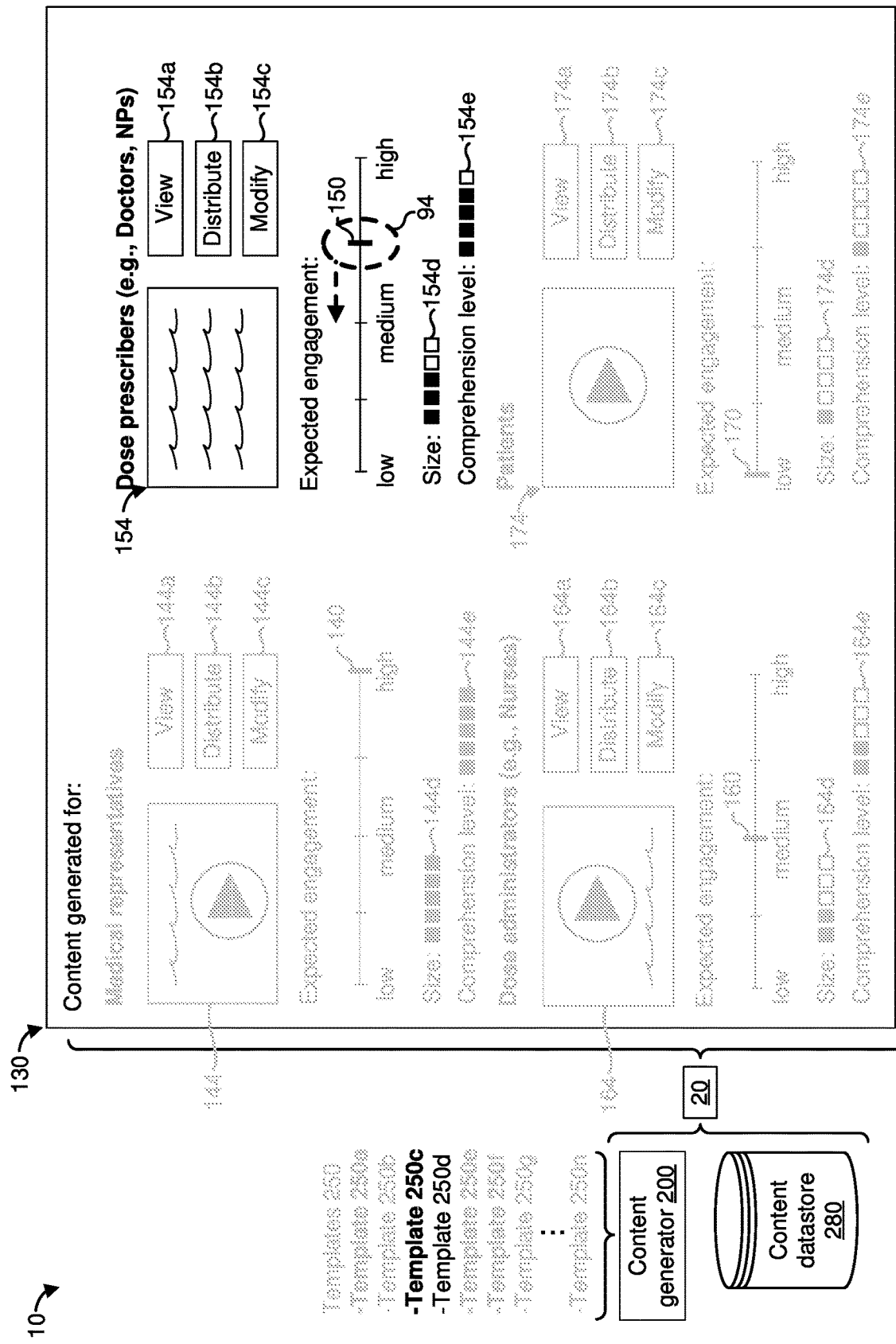
Figure 1E:
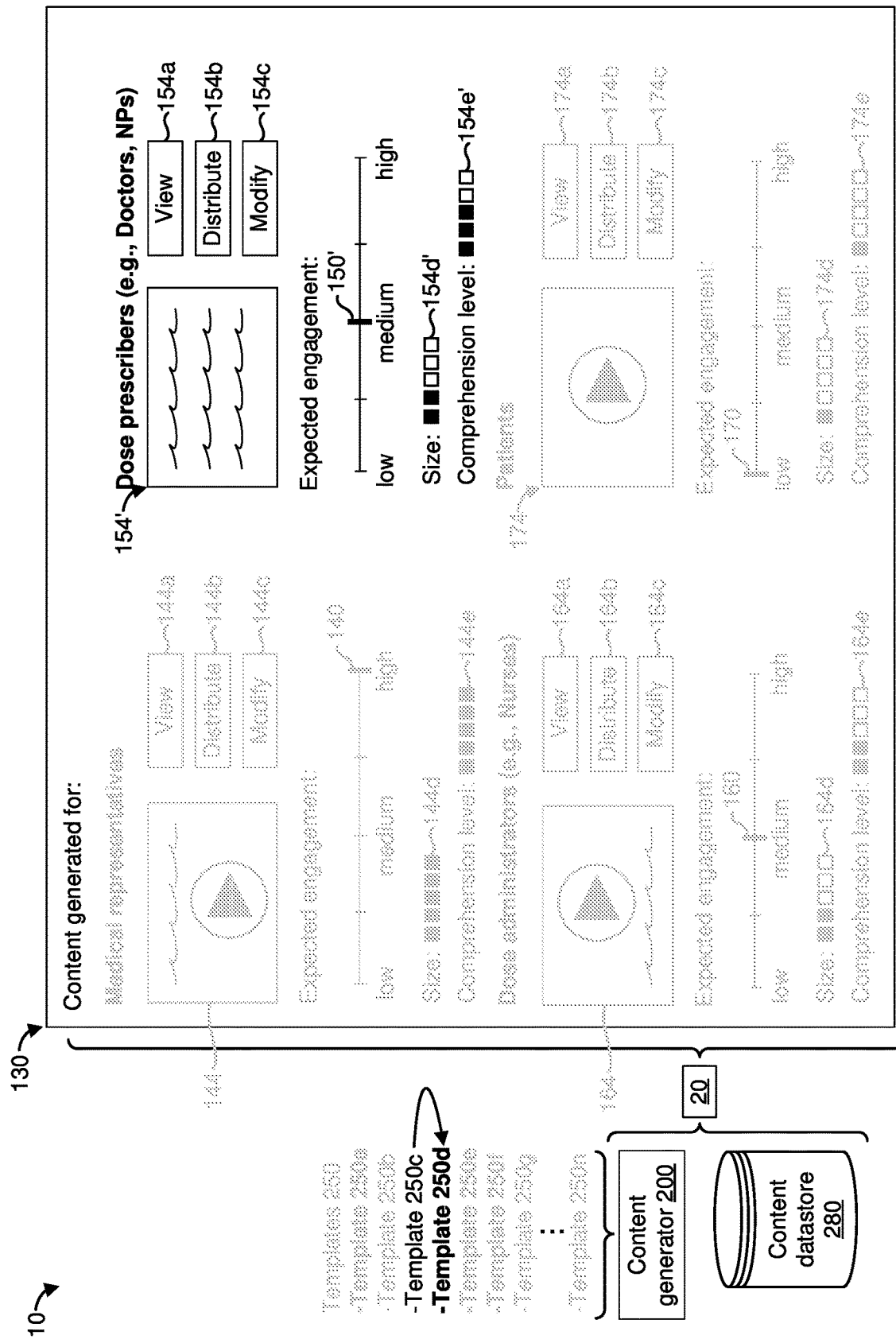

Referring to FIG. 1D, in some implementations, the content presentation GUI 130 allows a user of the device 20 to change the expected engagement value for a user type. Changing the expected engagement value to a new value for a user type triggers the device 20 to modify the media content item for the user type based on the new value. In the example of FIG. 1D, the device 20 detects a user input 94 (e.g., a drag input or a swipe input) that corresponds to a request to change the second expected engagement value 150. As shown in FIG. 1E, the user has lowered the second expected engagement value 150 to 'medium'.

Referring to FIG. 1E, in response to detecting that the second expected engagement value 150 has been changed to a modified second expected engagement value 150', the content generator 200 modifies the second media content item 154 in order to generate a modified second media content item 154'. In the example of FIG. 1E, the device 20 switches from the third template 250c to the fourth template 250d. While the second media content item 154 was generated by populating the third template 250c, the content generator 200 generates the modified second media content item 154' by populating the fourth template 250d with information from the content datastore 280. Since the third template 250c and the fourth template 250d may require different types or amounts of information, the modified second media content item 154' generated by populating the fourth template 250d may be different from the second media content item 154 (shown in FIG. 1D) generated by populating the third template 250c. For example, the modified second media content item 154' may include different information regarding the pharmaceutical article than the second media content item 154. As an example, the modified second media content item 154' may include less information relative to the second media content item 154, for example, because the modified second expected engagement value 150' is less than the second expected engagement value 150.

In some implementations, the modified second media content item 154' is associated with a modified second size indicator 154d' that indicates a modified second size value that is less than the second size value indicated by the second size indicator 154d shown in FIG. 1D. More generally, in some implementations, changing the expected engagement value for a user type results in the generation of a modified media content item of a different size. In some implementations, the modified second media content item 154' is associated with a modified second comprehension level indicator 154e' that indicates a modified second comprehension level that is different from the second comprehension level indicated by the second comprehension level indicator 154e shown in FIG. 1D. More generally, in some implementations, changing the expected engagement value for a user type results in the generation of a modified media content item that is associated with a different comprehension level.

Figure 1F:
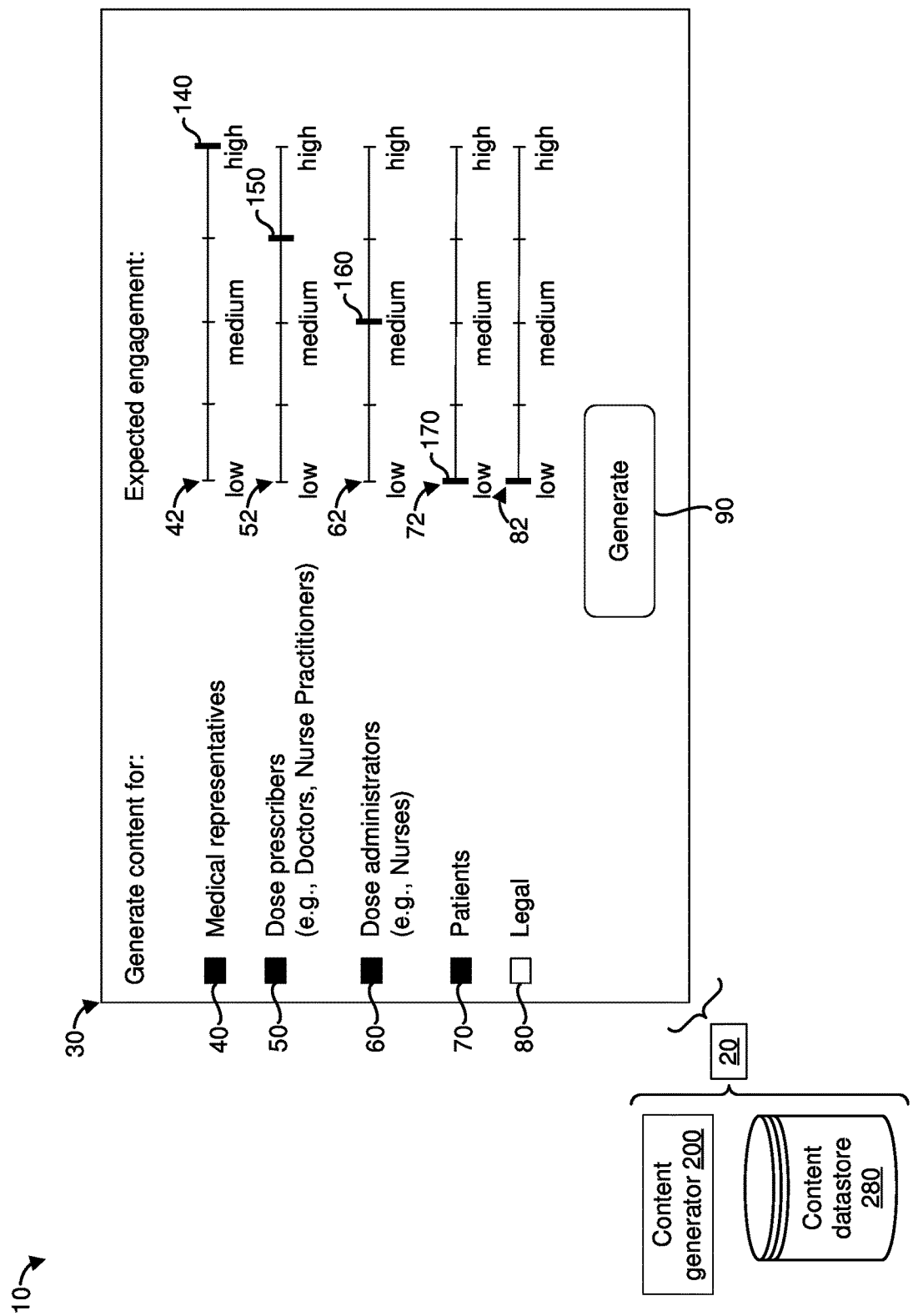

Referring to FIG. 1F, in some implementations, the content generation GUI 30 includes affordances that allow a user of the device 20 to specify expected engagement values for various user types when the user is submitting his/her request to generate media content items for the user types. As shown in FIG. 1F, in some implementations, the content generation GUI 30 includes a first engagement affordance 42 that allows the user of the device 20 to specify the first expected engagement value 140 for a first user type (e.g., for the medical representatives), a second engagement affordance 52 that allows the user to specify the second expected engagement value 150 for a second user type (e.g., for the dose prescribers), a third engagement affordance 62 that allows the user to specify the third expected engagement value 160 for a third user type (e.g., for the dose administrators), a fourth engagement affordance 72 that allows the user to specify the fourth expected engagement value 170 for a fourth user type (e.g., for the patients), and a fifth engagement affordance 82 that allows the user to specify a fifth expected engagement value for a fifth user type (e.g., for legal persons).

Figure 1G:
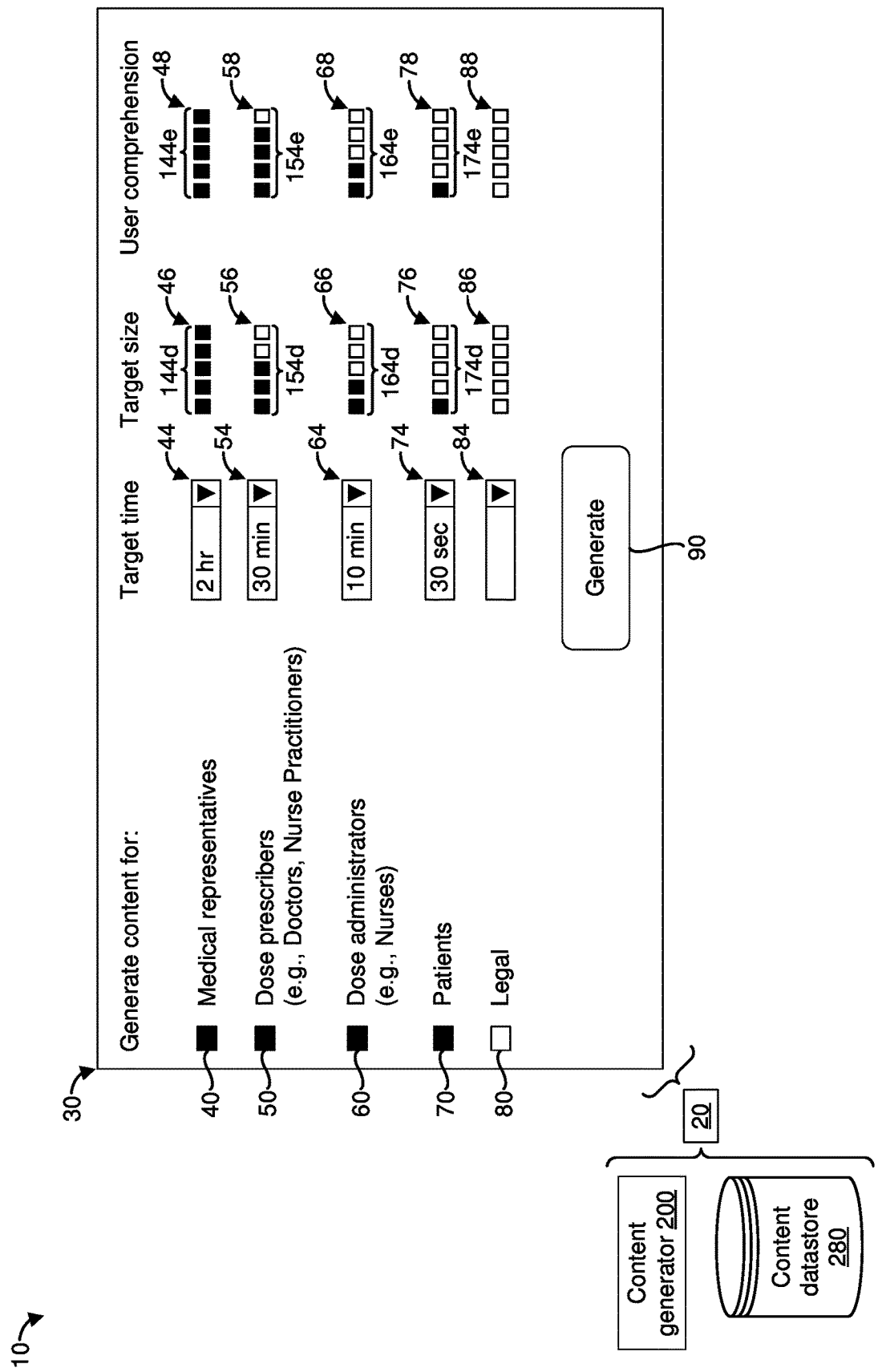

Referring to FIG. 1G, in some implementations, the content generation GUI 30 includes affordances that allow a user of the device 20 to specify target time durations (e.g., expected time durations) for various user types to view their corresponding media content items. For example, the content generation GUI 30 includes a first time affordance 44 for specifying a first amount of time that medical representatives are expected to view a corresponding first media content item for (e.g., for 2 hours), a second time affordance 54 for specifying a second amount of time that dose prescribers are expected to view a corresponding second media content item for (e.g., for 30 minutes), a third time affordance 64 for specifying a third amount of time that dose administrators are expected to view a corresponding third media content item for (e.g., for 10 minutes), a fourth time affordance 74 for specifying a fourth amount of time that patients are expected to view a corresponding fourth media content item for (e.g., for 30 seconds), and a fifth time affordance 84 for specifying a fifth amount of time that legal persons are expected to view a corresponding fifth media content item for. In some implementations, the templates 250 that the content generator 200 selects for generating the media content items 144, 154, 164 and 174 (shown in FIG. 1C) are based on the values specified via the time affordances 44, 54, 64 and 74, respectively.

In some implementations, the content generation GUI 30 includes affordances that allow a user of the device 20 to specify target size values (e.g., maximum size values) for media content items that correspond to the various user types. For example, the content generation GUI 30 includes a first target size affordance 46 for specifying a first target size for the first media content item 144 (shown in FIG. 1C), a second target size affordance 56 for specifying a second target size for the second media content item 154 (shown in FIG. 1C), a third target size affordance 66 for specifying a third target size for the third media content item 164 (shown in FIG. 1C), a fourth target size affordance 76 for specifying a fourth target size for the fourth media content item 174 (shown in FIG. 1C), and a fifth target size affordance 86 for specifying a fifth target size for a fifth media content item for legal persons. In some implementations, the templates 250 that the content generator 200 selects for generating the media content items 144, 154, 164 and 174 (shown in FIG. 1C) are based on the values specified via the target size affordances 46, 56, 66 and 76, respectively. In some implementations, the size values indicated by the size indicators 144*d*, 154*d*, 164*d* and 174*d* correspond to (e.g., are same as) the size values specified via the target size affordances 46, 56, 66 and 76, respectively.

In some implementations, the content generation GUI 30 includes affordances that allow a user of the device 20 to specify target comprehension level values (e.g., required comprehension level values, desired comprehension levels or maximum comprehension levels) for media content items that correspond to the various user types. For example, the content generation GUI 30 includes a first comprehension affordance 48 for specifying a first target comprehension level for the first media content item 144 (shown in FIG. 1C), a second comprehension affordance 58 for specifying a second target comprehension level for the second media content item 154 (shown in FIG. 1C), a third comprehension affordance 68 for specifying a third target comprehension level for the third media content item 164 (shown in FIG. 1C), a fourth comprehension affordance 78 for specifying a fourth target comprehension level for the fourth media content item 174 (shown in FIG. 1C), and a fifth comprehension affordance 88 for specifying a fifth target comprehension level for a fifth media content item for legal persons. In some implementations, the templates 250 that the content generator 200 selects for generating the media content items 144, 154, 164 and 174 (shown in FIG. 1C) are based on the values specified via the comprehension affordances 48, 58, 68 and 78, respectively. In some implementations, the comprehension level values indicated by the comprehension level indicators 144*e*, 154*e*, 164*e* and 174*e* correspond to (e.g., are same as) the comprehension values specified via the comprehension affordances 48, 58, 68 and 78, respectively.

Figure 2A:
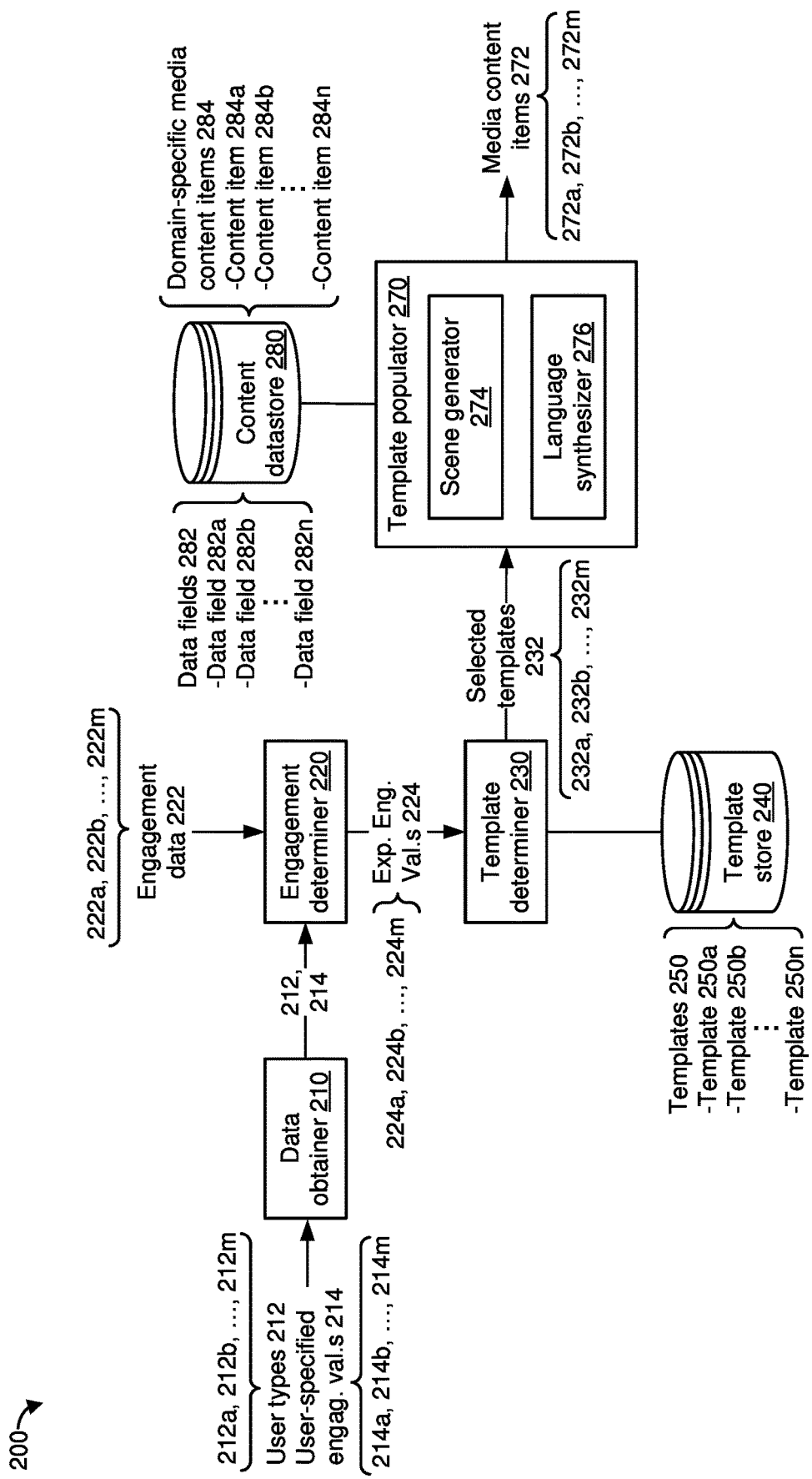
FIG. 2A is a block diagram of a content generator in accordance with some implementations.

FIG. 2A illustrates a block diagram of the content generator 200 in accordance with some implementations. In some implementations, the content generator 200 includes a data obtainer 210, an engagement determiner 220, a template determiner 230, a template store 240 that stores the templates 250, a template populator 270 and the content datastore 280.

In various implementations, the data obtainer 210 obtains a request to generate media content items for various user types 212 (e.g., a first user type 212*a*, a second user type 212*b*, . . . , and an mth user type 212*m*). In some implementations, the data obtainer 210 obtains an indication of the user types 212 by detecting values specified via the affordances 40, 50, 60, 70 and 80 shown in FIGS. 1A-1B and 1F-1G. In some implementations, the data obtainer 210 provides an indication of the user types 212 to the engagement determiner 220. In some implementations, the user types 212 are associated with corresponding user-specified engagement values 214 (e.g., a first user-specified engagement value 214*a* for the first user type 212*a*, a second user-specified engagement value 214*b* for the second user type 212*b*, and an mth user-specified engagement value 214*m* for the mth user type 214*m*). In some implementations, the data obtainer 210 obtains an indication of the user-specified engagement values 214 by detecting values specified via the engagement affordances 42, 52, 62, 72 and 82 shown in FIG. 1F. In some implementations, the data obtainer 210 obtains the user-specified engagement values 214 by detecting values specified via the time affordances 44, 54, 64, 74 and 84 shown in FIG. 1G. In some implementations, the data obtainer 210 obtains the user-specified engagement values 214 by detecting values specified via the target size affordances 46, 56, 66, 76 and 86 shown in FIG. 1G. In some implementations, the data obtainer 210 obtains the user-specified engagement values 214 by detecting values specified via the comprehension affordances 48, 58, 68, 78 and 88 shown in FIG. 1G. In some implementations, the data obtainer 210 provides the user-specified engagement values 214 to the engagement determiner 220.

In some implementations, the engagement determiner 220 determines corresponding expected engagement values 224 for the user types 212. For example, the engagement determiner 220 determines a first expected engagement value 224*a* for the first user type 212*a*, a second expected engagement value 224*b* for the second user type 212*b*, and an mth expected engagement value 224*m* for the mth user type 212*m*. In some implementations, the engagement determiner 220 determines the expected engagement values 224 based on the user-specified engagement values 214. In some implementations, the expected engagement values 224 are the same as the user-specified engagement values 214. In some implementations, the expected engagement values 224 are with a threshold of the user-specified engagement values 214. More generally, in various implementations, the expected engagement values 224 determined by the engagement determiner 220 are a function of the user-specified engagement values 214.

In some implementations, the engagement determiner 220 obtains engagement data 222 that indicates prior engagement of users of the user types 212 with information related to the domain associated with the request. For example, in some implementations, the engagement data 222 includes first engagement data 222*a* that indicates prior engagement of users of the first user type 212*a* with information related to pharmaceutical articles, second engagement data 222*b* that indicates prior engagement of users of the second user type 212*b* with information related to pharmaceutical articles, . . . , and mth engagement data 222*m* that indicates prior engagement of users of the mth user type 212*m* with information related to pharmaceutical articles. In some implementations, the prior engagement is based on media content items that users have previously engaged with (e.g., viewed, listened to, commented on and/or written). In some implementations, the engagement data 222 is domain-specific. For example, the engagement data 222 may characterize prior engagement with content that relates to various pharmaceutical articles (e.g., various pharmaceutical drugs and/or medical devices) that are in a pharmacology domain. In some implementations, the engagement data 222 is subject-specific (e.g., specific to a particular pharmaceutical article). For example, the engagement data 222 may characterize prior engagement with content that relates to a particular pharmaceutical article (e.g., a particular pharmaceutical drug such as a blood glucose reducing medication, or a particular medical device such as an insulin delivery device).

In various implementations, the engagement determiner 220 determines the expected engagement values 224 based on the engagement data 222. For example, in some implementations, the engagement determiner 220 determines the first expected engagement value 224*a* based on the first engagement data 222*a*, the second expected engagement value 224*b* based on the second engagement data 222*b*, . . . , and the mth expected engagement value 224*m* based on the mth engagement data 222*m*.

In some implementations, the engagement data 222 indicates amounts of prior engagement (e.g., time durations of prior engagement) with a domain associated with the request or with a subject of the request. For example, if the request relates to a particular pharmaceutical drug, the engagement data 222 may indicate amounts of prior engagement with information related to pharmaceutical drugs in general, with information related to a class (e.g., a type) of pharmaceutical drugs to which the particular pharmaceutical drug belongs or with information related to that particular pharmaceutical drug. In some implementations, the first engagement data 222a indicates a first amount of prior engagement (e.g., a first time duration of prior engagement) of the first user type 212a with the domain or the subject associated with the request, the second engagement data 222b indicates a second amount of prior engagement (e.g., a second time duration of prior engagement) of the second user type 212b with the domain or the subject associated with the request, . . . , and the mth engagement data 222m indicates an mth amount of prior engagement (e.g., an mth time duration of prior engagement) of the mth user type 212m with the domain or the subject associated with the request. In various implementations, the engagement determiner 220 determines the expected engagement values 224 based on the amounts of prior engagement indicated by the engagement data 222. For example, in some implementations, the expected engagement values 224 of the various user types 212 are proportional (e.g., directly proportional or inversely proportional) to the amounts of prior engagement of the user types 212 with the domain or the subject associated with the request. As an example, if medical representatives have previously engaged with pharmaceutical content for more than a threshold amount of time, the expected engagement value 224 for medical representatives indicates that the medical representatives are expected to engage with content for a new pharmaceutical drug for more than the threshold amount of time.

In some implementations, the engagement data 222 indicates comprehension levels of prior engagement (e.g., levels of complexity or levels of difficulty of previously engaged content) with a domain associated with the request or with a subject of the request. For example, if the request relates to a particular pharmaceutical drug, the engagement data 222 may indicate comprehension levels of information related to pharmaceutical drugs that the user types 212 previously engaged with, comprehension levels of information related to a class (e.g., a type) of pharmaceutical drugs that the user types 212 previously engaged with or comprehension levels of information related to that particular pharmaceutical drug that the user types 212 previously engaged with. In some implementations, the first engagement data 222a indicates a first comprehension level (e.g., a first level of complexity or a first level of difficulty) of information related to the domain or the subject of the request that the first user type 212a engaged with, the second engagement data 222b indicates a second comprehension level (e.g., a second level of complexity or a second level of difficulty) of information related to the domain or the subject of the request that the second user type 212b engaged with, . . . , and the mth engagement data 222m indicates an mth comprehension level (e.g., an mth level of complexity or an mth level of difficulty) of information related to the domain or the subject of the request that the mth user type 212m engaged with. In various implementations, the engagement determiner 220 determines the expected engagement values 224 based on the comprehension levels indicated by the engagement data 222. For example, in some implementations, the expected engagement values 224 of the various user types 212 are proportional (e.g., directly proportional or inversely proportional) to the comprehension levels of information that the user types 212 previously engaged with. As an example, if medical representatives have previously engaged with pharmaceutical content with a comprehension level that is greater than a threshold comprehension level, the expected engagement value 224 for medical representatives indicates that the medical representatives are expected to engage with content with a comprehension level that is greater than the threshold comprehension level.

In some implementations, the engagement data 222 indicates modalities of prior engagement with information related to a domain or a subject associated with the request. For example, in some implementations, the engagement data 222 indicates whether the prior engagement was with textual content (e.g., research papers, clinical studies, etc.), video content (e.g., seminars, advertisements, etc.) or audio content (e.g., podcasts, radio commercials, etc.). For example, if the request relates to a particular medical device, the engagement data 222 may indicate modalities of information related to medical devices that the user types 212 previously engaged with, modalities of information related to a class (e.g., a type) of medical devices that the user types 212 previously engaged with or modalities of information related to that particular medical device that the user types 212 previously engaged with. In some implementations, the first engagement data 222a indicates a first set of modalities (e.g., text and video) of information related to the domain or the subject of the request that the first user type 212a engaged with, the second engagement data 222b indicates a second set of modalities (e.g., text) of information related to the domain or the subject of the request that the second user type 212b engaged with, . . . , and the mth engagement data 222m indicates an mth set of modalities (e.g., video) of information related to the domain or the subject of the request that the mth user type 212m engaged with. In various implementations, the engagement determiner 220 determines the expected engagement values 224 based on the modalities indicated by the engagement data 222. In some implementations, the expected engagement values 224 indicate preferred modalities for the user types 212, and the preferred modalities are the same as the previous modalities indicated by the engagement data 222. As an example, if medical representatives have previously engaged with pharmaceutical content via text and video, the expected engagement value 224 for medical representatives indicates that the medical representatives are expected to (e.g., prefer to) view videos and read text. As another example, if dose prescribers have previously engaged with pharmaceutical content via text, the expected engagement value 224 for dose prescribers indicates that the dose prescribers are expected to (e.g., prefer to) read text.

In various implementations, the template determiner 230 determines templates for the user types 212 based on the expected engagement values 224. In some implementations, the template determiner 230 determines the templates for the user types 212 by selecting a subset 232 of the templates 250 ("selected templates 232", hereinafter for the sake of brevity) based on the expected engagement values 224. In some implementations, the selected templates 232 include a first selected template 232a that the template determiner 230 selects for the first user type 212a based on the first expected engagement value 224a, a second selected template 232b that the template determiner 230 selects for the second user type 212b based on the second expected engagement value 224b, . . . , and an mth selected template 232m that the template determiner 230 selects for the mth user type 212m based on the mth expected engagement value 224m.

In some implementations, the templates 250 are associated with different amounts of information. For example, in some implementations, the templates 250 include different numbers of display elements (e.g., data fields or GUI elements such as textboxes, etc.). In some implementations, the expected engagement values 224 indicate expected amounts of engagement (e.g., expected time durations of engagement), and the template determiner 230 selects the selected templates 232 based on the expected amounts of engagement. For example, the template determiner 230 selects the selected templates 232 such that the selected templates 232 can be populated with amounts of information that match the expected amounts of engagement.

In some implementations, the templates 250 are associated with different comprehension levels. In some implementations, the expected engagement values 224 indicate expected comprehension levels, and the template determiner 230 selects the selected templates 232 based on the expected comprehension levels. For example, the template determiner 230 selects the selected templates 232 such that the selected templates 232 can be populated with information that is associated with the expected comprehension levels.

In some implementations, the templates 250 are associated with different sets of modalities. For example, some of the templates 250 may include display elements (e.g., GUI elements) that can be populated with textual content and video content while other templates 250 may include display elements for textual content but not video content. In some implementations, the expected engagement values 224 indicate expected modalities, and the template determiner 230 selects the selected templates 232 based on the expected modalities. For example, the template determiner 230 selects the selected templates 232 such that the selected templates 232 can be populated with information that is associated with the expected modalities.

In some implementations, the template determiner 230 synthesizes a new template. In some implementations, the template determiner 230 synthesizes a new template when the templates 250 in the template store 240 are not suitable for one of the user types 212. In some implementations, the template determiner 230 synthesizes a new template when the templates 250 in the template store 240 are not suitable for the expected engagement values 224. In some implementations, the template determiner 230 synthesizes the new template by modifying one of the templates 250 stored in the template store 240 based on the expected engagement values 224. For example, the template determiner 230 may truncate one of the templates 250 based on one of the expected engagement values 224 being below a threshold engagement value. In some implementations, the template determiner 230 synthesizes the new template by combining two or more of the templates 250 in the template store 240. For example, the template determiner 230 may concatenate portions of two or more of the templates 250 based on one of the expected engagement values 224 being greater than a threshold engagement value.

In various implementations, the template populator 270 generates corresponding media content items 272 (e.g., the media content items 144, 154, 164 and 174 shown in FIG. 1C) for the user types 212 by populating the selected templates 232 with information stored in the content datastore 280. For example, the template populator 270 generates a first media content item 272a for the first user type 212a by populating the first selected template 232a, a second media content item 272b for the second user type 212b by populating the second selected template 232b, . . . , and an mth media content item 272m for the mth user type 212m by populating the mth selected template 232m.

In various implementations, the content datastore 280 includes a relational database with a set of data fields 282 (e.g., a first data field 282a, a second data field 282b, an nth data field 282n) that store respective values. In some implementations, the template populator 270 generates the media content items 272 by populating the selected templates 232 with some of the values stored in the data fields 282.

In some implementations, the content datastore 280 stores a set of existing domain-specific media content items 284 (e.g., a first existing content item 284a, a second existing content item 284b, . . . , and an nth existing content item 284n). In some implementations, the template populator 270 generates the media content items 272 by extracting information from the domain-specific media content items 284 and populating the selected templates 232 with information extracted from the domain-specific media content items 284. In some implementations, the data fields 282 store information that is extracted from the domain-specific media content items 284.

In some implementations, the template populator 270 includes a scene generator 274 that synthesizes a new scene (e.g., a description of the new scene or a new video depicting the new scene) based on the information stored in the content datastore 280. In some implementations, at least one of the selected templates 232 is to be populated with a video, and the scene generator 274 generates the video so that the template populator 270 can populate the selected template 232 with the generated video. In some implementations, the selected template 232 specifies a plot (e.g., a storyline) for the video (e.g., an advertisement), and the scene generator 274 generates a video that satisfies the plot. For example, in some implementations, the selected template 232 specifies that the video is to include a person who is experiencing back pain and the person takes a medication to alleviate the back pain. In this example, the scene generator 274 generates a video that includes a representation of a person expressing back pain and taking the medication to alleviate the back pain. In some implementations, the scene generator 274 includes a neural network system (e.g., a set of one or more neural networks) that generate the scene. In such implementations, the neural network system obtains requirements for a scene from a selected template 232 and information from the content datastore 280 as inputs, and outputs a generated scene.

In some implementations, the template populator 270 includes a language synthesizer 276 (e.g., a sentence synthesizer) that synthesizes new sentences based on the information stored in the content datastore 280. In some implementations, at least one of the selected templates 232 is to be populated with text that includes proper grammar sentences. In such implementations, the language synthesizer 276 synthesizes the sentences based on information retrieved from the content datastore 280. In some implementations, the language synthesizer 276 includes a neural network system (e.g., a set of one or more neural networks) that synthesizes the sentences.

Figure 2B:
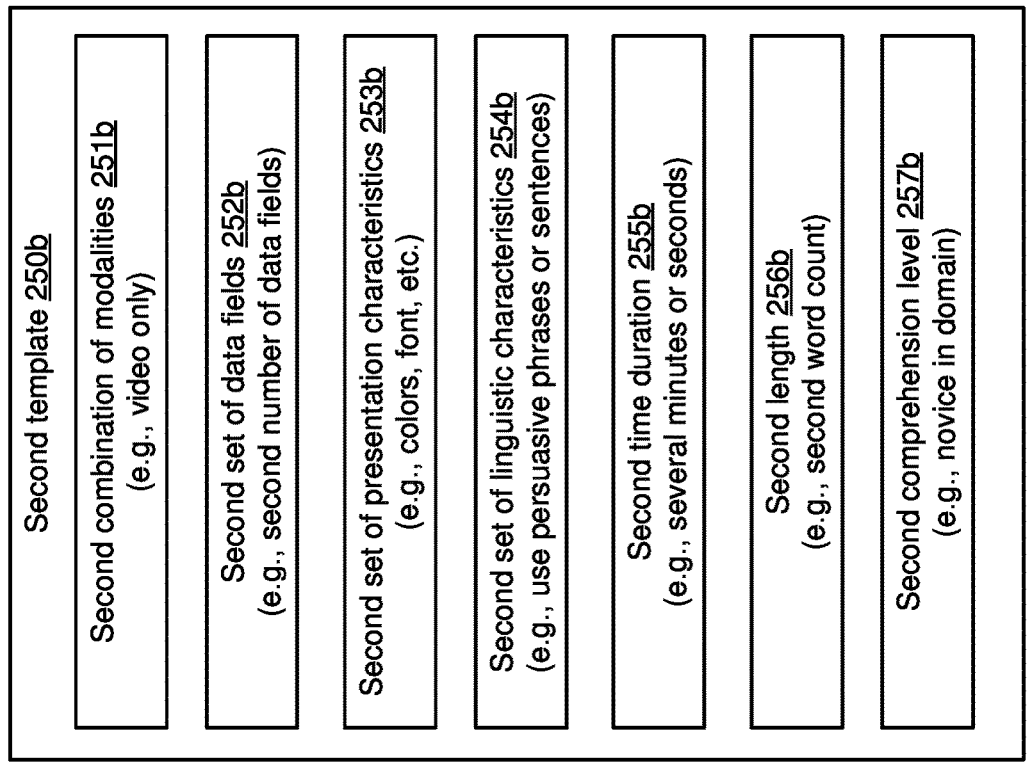
FIG. 2B is a block diagram of example templates in accordance with some implementations.

FIG. 2B is a block diagram of example templates in accordance with some implementations. As illustrated in FIG. 2B, in some implementations, the first template 250a specifies that the first template 250a includes display elements (GUI elements) for a first combination of modalities 251a (e.g., text and video). In the example of FIG. 2B, the first template 250a can be populated with information that is associated with at least one of the first combination of modalities 251a. By contrast, the second template 250b specifies that the second template 250b includes display elements for a second combination of modalities 251b (e.g., video only). In the example of FIG. 2B, the second template 250b can be populated with information that is associated with the second combination of modalities 251b. As can be seen in FIG. 2B, in some implementations, the templates 250 may be associated with different modalities. Example modalities include text, video, audio and haptic responses (e.g., vibrations).

In some implementations, the first template 250a includes a first set of data fields 252a (e.g., a first set of display elements, for example, a first set of GUI elements) that can be populated with information, and the second template 250b includes a second set of data fields 252b (e.g., a second set of display elements, for example, a second set of GUI elements) that can be populated with information. The first set of data fields 252a may include a first number of data fields, and the second set of data fields 252b may include a second number of data fields that is different from the first number of data fields. More generally, in various implementations, the templates 250 can accommodate different amounts of information.

In some implementations, the first template 250a specifies a first set of presentation characteristics 253a, and the second template 250b specifies a second set of presentation characteristics 253b. In some implementations, the first set of presentation characteristics 253a may be different from the second set of presentation characteristics 253b. In some implementations, the first set of presentation characteristics 253a includes a first layout, and the second set of presentation characteristics 253b includes a second layout that is different from the first layout. In some implementations, the first set of presentation characteristics 253a specifies a first set of colors, a first set of fonts, etc. In some implementations, the second set of presentation characteristics 253b specifies a second set of colors, a second set of fonts, etc. More generally, in various implementations, the templates 250 utilize different presentation characteristics to present information regarding a subject.

In some implementations, the first template 250a is associated with a first set of linguistic characteristics 254a, and the second template 250b is associated with a second set of linguistic characteristics 254b that are different from the first set of linguistic characteristics 254a. In some implementations, the first set of linguistic characteristics 254a includes a first type of phrases (e.g., objective phrases), and the second set of linguistic characteristics 254b includes a second type of phrases that are different from the first type of phrases (e.g., persuasive phrases). In some implementations, the first set of linguistic characteristics 254a specifies that the first template 250a is to be populated with sentences having a first type of sentence structure (e.g., informal sentences such as bullet points), and the second set of linguistic characteristics 254b specifies that the second template 250b is to be populated with sentences having a second type of sentence structure (e.g., formal sentences with proper grammar and punctuation).

In some implementations, the first template 250a is associated with a first time duration 255a, and the second template 250b is associated with a second time duration 255b that is different from the first time duration 255a. For example, in some implementations, the first template 250a is for content that a user is expected to finish reviewing over the course of several days or hours (e.g., a multi-day course on a pharmaceutical article), and the second template 250b is for content that a user is expected to finish reviewing over the course of several minutes or seconds (e.g., an advertisement for a pharmaceutical article or a brochure for a pharmaceutical article).

In some implementations, the first template 250a is associated with a first length 256a, and the second template 250b is associated with a second length 256b that is different from the first length 256a. For example, in some implementations, the first template 250a is for content that spans a first word count, a first page count or a first temporal length, and the second template 250b is for content that spans a second word count, a second page count or a second temporal length.

In some implementations, the first template 250a is associated with a first comprehension level 257a, and the second template 250b is associated with a second comprehension level 257b that is different from the first comprehension level 257a. For example, in some implementations, the first template 250a is for content that is suitable for an expert in a domain (e.g., for expert medical representatives, for example, for medical representatives with more than 20 years of experience in representing pharmaceutical articles), and the second template 250b is for content that is suitable for a novice in the domain (e.g., for novice medical representatives, for example, for medical representatives with less than 2 years of experience in representing pharmaceutical articles).

Figure 2B:
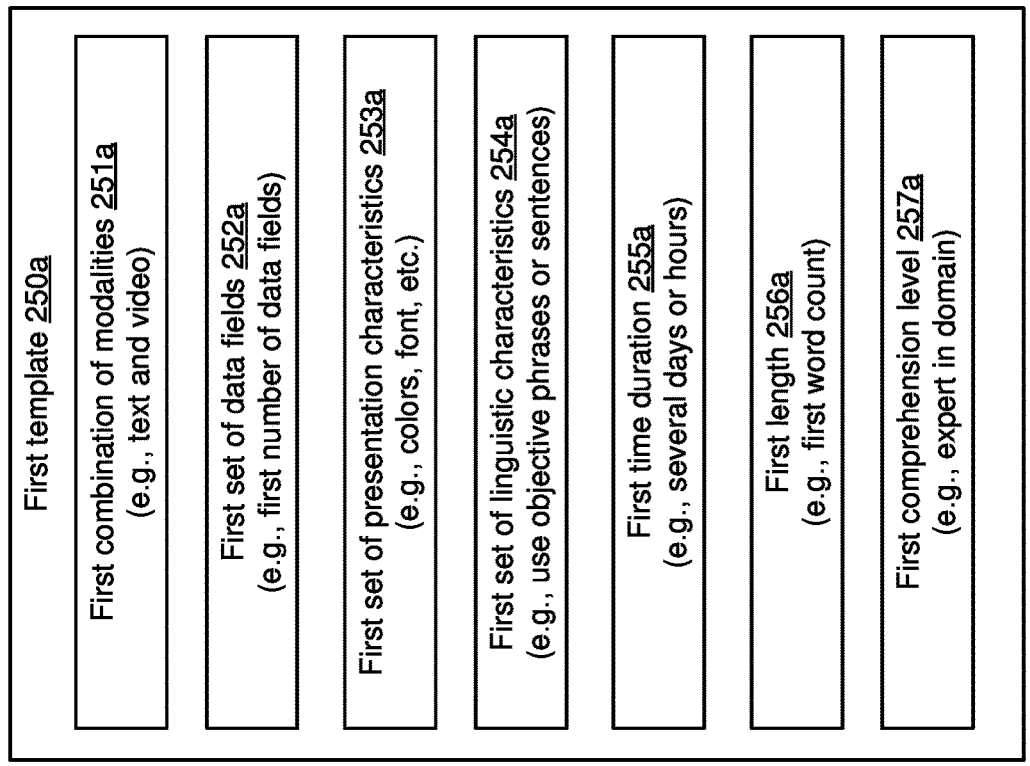
Figure 3:
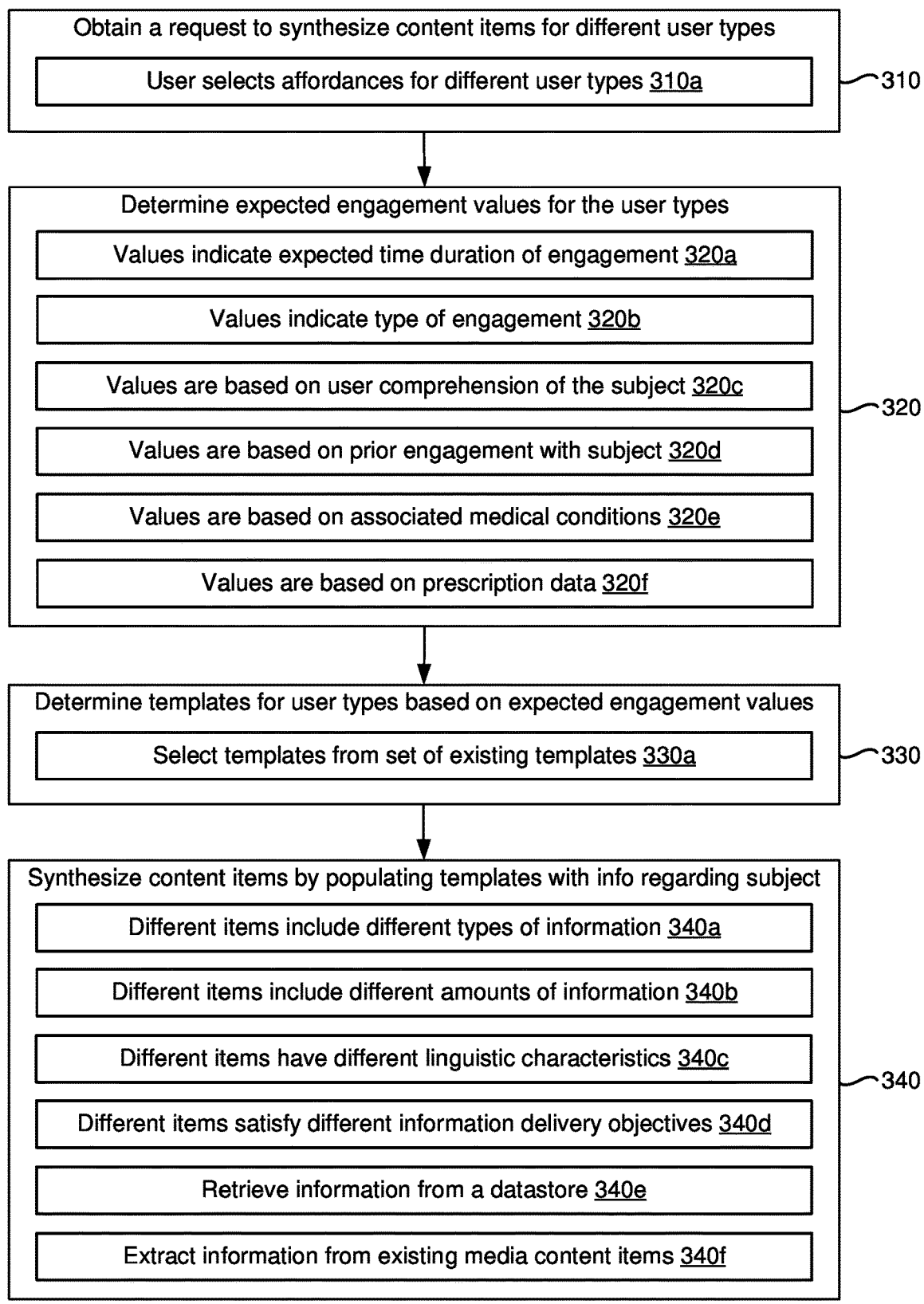
FIG. 3 is a flowchart representation of a method of generating content for different user types in accordance with some implementations.

FIG. 3 is a flowchart representation of a method 300 of generating content for different user types in accordance with some implementations. In various implementations, the method 300 is performed by a device including a non-transitory memory and a processor coupled with the non-transitory memory (e.g., the device 20 shown in FIGS. 1A-1G, and/or the content generator 200 shown in FIGS. 1A-2). In some implementations, the method 300 is performed by processing logic, including hardware, firmware, software, or a combination thereof. In some implementations, the method 300 is performed by a processor executing code stored in a non-transitory computer-readable medium (e.g., a memory). In some implementations, the method 300 is performed at a server or a cloud computing platform.

As represented by block 310, in various implementations, the method 300 includes obtaining a request to synthesize a plurality of pharmaceutical content items for respective user types. In some implementations, the plurality of pharmaceutical content items provides information regarding a pharmaceutical article. In some implementations, the pharmaceutical article includes a pharmaceutical drug (e.g., a medication). In some implementations, the pharmaceutical article includes a medical device. For example, as shown in FIG. 2A, the data obtainer 210 obtains a request that specifies the user types 212.

As represented by block 310a, in some implementations, obtaining the request comprises detecting a first user input selecting a first affordance that corresponds to a first one of the respective user types, and detecting a second user input selecting a second affordance that corresponds to a second one of the respective user types. For example, as shown in FIG. 1B, the user of the device 20 selects the first affordance 40 (e.g., the first checkbox) for medical representatives, the second affordance 50 (e.g., the second checkbox) for dose prescribers, the third affordance 60 (e.g., the third checkbox) for dose administrators, and the fourth affordance 70 (e.g., the fourth checkbox) for patients.

In some implementations, obtaining the request includes receiving user-specified engagement values for the respective user types. For example, as shown in FIG. 2A, the data obtainer 210 receives the user-specified engagement values 214 for the user types 212. As illustrated in FIG. 1F, in some implementations, the device obtains the user-specified engagement values via the engagement affordances 42, 52, 62, 72 and 82. In some implementations, the user-specified engagement values include expected time duration values (e.g., the time duration values provided via the time affordances 44, 54, 64, 74 and 84 shown in FIG. 1G). In some implementations, the user-specified engagement values include target size values for the requested media content items (e.g., the target size values provided via the target size affordances 46, 56, 66, 76 and 86 shown in FIG. 1G). In some implementations, the user-specified engagement values include target comprehension levels for the requested media content items (e.g., the target comprehension levels provided via the comprehension affordances 48, 58, 68, 78 and 88 shown in FIG. 1G). In some implementations, the method 300 includes displaying a prompt that prompts a user of the device to provide the user-specified engagement values.

As represented by block 320, in various implementations, the method 300 includes determining, for the respective user types, corresponding expected engagement values indicative of expected engagement with the pharmaceutical article. For example, as shown in FIG. 2A, the engagement determiner 220 determines the corresponding expected engagement values 224 for the user types 212. As another example, as shown in FIG. 1C, the content generator 200 determines the expected engagement values 140, 150, 160 and 170 for the medical representatives, the dose prescribers, the dose administrators and the patients, respectively.

As represented by block 320a, in some implementations, the corresponding expected engagement values include a first expected time duration value for a first user type of the respective user types and a second expected time duration value for a second user type of the respective user types. For example, patients may be expected to engage with their pharmaceutical content item regarding the pharmaceutical article for less than two minutes, for example, for the duration of a TV commercial. By contrast, doctors may be expected to engage with their pharmaceutical content item regarding the pharmaceutical article for several hours, for example, the doctors may be expected to read results of clinical studies. As shown in FIG. 1G, the respective target time durations for medical representatives and dose prescribers are different. In some implementations, determining the respective content templates includes determining, for the first user type, a first content template of a first length (e.g., a first spatial length or a first temporal length) that is a function of the first expected time duration value. In some implementations, determining the respective content templates includes determining, for the second user type, a second content template of a second length (e.g., a second spatial length or a second temporal length) that is a function of the second expected time duration value. In some implementations, the second length is different from the first length. For example, as shown in FIG. 2B, the first template 250a is associated with the first time duration 255a and/or the first length 256a, and the second template 250b is associated with the second time duration 255b and/or the second length 256b.

As represented by block 320b, in some implementations, the corresponding expected engagement values indicate a first expected modality for a first user type of the respective user types and a second expected modality for a second user type of the respective user types. For example, patients may be expected to watch a video, for example, a commercial. By contrast, physicians may be expected to read text, for example, results of clinical studies. In some implementations, determining the respective content templates includes determining, for the first user type, a first content template with a first layout that is a function of the first expected modality. In some implementations, determining the respective content templates includes determining, for the second user type, a second content template with a second layout that is a function of the second expected modality. In some implementations, the second layout is different from the first layout. In some implementations, the first layout is more suitable for the first expected modality than the second layout. Similarly, in some implementations, the second layout is more suitable for the second expected modality than the first layout. For example, as shown in FIG. 2B, the first template 250a is associated with the first combination of modalities 251a (e.g., text and video), and the second template 250b is associated with the second combination of modalities 251b (e.g., video).

As represented by block 320c, in some implementations, the corresponding expected engagement values include a first user comprehension value indicative of an estimated comprehension level of a first user type of the respective user types regarding the pharmaceutical article and a second user comprehension value indicative of an estimated comprehension level of a second user type of the respective user types regarding the pharmaceutical article. For example, in some implementations, the expected engagement of patients with a pharmaceutical content item that provides information regarding a pharmaceutical article is proportional to comprehension levels of patients regarding pharmaceuticals in general. For example, the more a patient knows about drugs, the more the patient is expected to engage with informational materials for a particular drug. In some implementations, the expected engagement is inversely proportional to estimated comprehension levels. For example, the less a doctor knows about a drug, the more likely the doctor is to engage with informational materials for the drug. In some implementations, the method 300 includes estimating user comprehension levels based on education levels or training levels. As an example, as shown in FIG. 1C, the content generator 200 determines the comprehension levels indicated by the comprehension level indicators 144e, 154e, 164e and 174e. In some implementations, determining the respective content templates includes determining, for the first user type, a first content template with a first set of data fields (e.g., a first number of data fields) that is a function of the first user comprehension value. In some implementations, determining the respective content templates includes determining, for the second user type, a second content template with a second set of data fields (e.g., a second number of data fields) that is a function of the second user comprehension value. In some implementations, the second set of data fields is different from the first set of data fields. For example, the second number of data fields is different from the first number of data fields. In some implementations, the data fields include display elements (e.g., GUI elements such as text boxes) that can be populated with information. As an example, as shown in FIG. 2B, the first template 250a includes the first set of data fields 252a and the second template 250b includes the second set of data fields 252b.

As represented by block 320d, in some implementations, the corresponding expected engagement values indicate, for a first user type of the respective user types, a first level of prior engagement with pharmaceutical content items that relate to a pharmaceutical domain associated with the pharmaceutical article (e.g., a first level of prior engagement with pharmaceutical content items that provide information regarding other comparable pharmaceutical articles that treat the same medical condition as the pharmaceutical article). In some implementations, the corresponding expected engagement values indicate, for a second user type of the respective user types, a second level of prior engagement with pharmaceutical content items that relate to the pharmaceutical domain (e.g., a second level of prior engagement with pharmaceutical content items that provide information regarding other comparable pharmaceutical articles that treat the same medical condition as the pharmaceutical article). In some implementations, the pharmaceutical domain refers to a corpus of information related to a medical condition that the pharmaceutical article treats. For example, as described in relation to FIG. 2A, in some implementations, the first expected engagement value 224*a* indicates a first level of prior engagement of the first user type 212*a* with media content items related to a subject, and the second expected engagement value 224*b* indicates a second level of prior engagement of the second user type 212*b* with media content items related to the subject. As an example, if the engagement data 222 indicates that physicians in the past have read about drugs that relate to diabetes management, the expected engagement of physicians with a media content item that provides information regarding a particular diabetes management drug is relatively high. In some implementations, determining the respective content templates includes determining, for the first user type, a first content template with a first set of data fields (e.g., a first number of GUI elements) that is a function of the first level of prior engagement. In some implementations, determining the respective content templates includes determining, for the second user type, a second content template with a second set of data fields (e.g., a second number of GUI elements) that is a function of the second level of prior engagement. As an example, the device can select the first template 250*a* (shown in FIG. 2B) with the first set of data fields 252*a* for the first user type based on the first level of prior engagement, and the second template 250*b* with the second set of data fields 252*b* for the second user type based on the second level of prior engagement. In some implementations, if the level of prior engagement is relatively high (e.g., greater than a threshold), the content template does not include GUI elements that the device populates with background information regarding the pharmaceutical domain. In some implementations, if the level of prior engagement is relatively low (e.g., less than a threshold), the content template includes GUI elements that the device populates with background information regarding the pharmaceutical domain.

As represented by block 320*e*, in some implementations, the pharmaceutical article is used to treat a medical condition. In some implementations, the corresponding expected engagement values include a first expected engagement value, for a first user type of the respective user types, based on a first type of association of the first user type with the medical condition. For example, the first user type may include patients that have the medical condition. In some implementations, the corresponding expected engagement values include a second expected engagement value, for a second user type of the respective user types, based on a second type of association of the second user type with the medical condition. For example, the second user type may include clinicians that treat the medical condition. In some implementations, determining the respective content templates includes determining, for the first user type, a first content template with a first set of data fields (e.g., a first number of GUI elements) that is a function of the first type of association with the medical condition. In some implementations, determining the respective content templates includes determining, for the second user type, a second content template with a second set of data fields (e.g., a second number of GUI elements) that is a function of the second type of association with the medical condition. For example, in some implementations, the device selects the first template 250*a* (shown in FIG. 2B) with the first set of data fields 252*a* for patients that have a medical condition, and the second template 250*b* with the second set of data fields 252*b* for clinicians that treat the medical condition. More generally, in various implementations, the content templates for patients and clinicians are different.

As represented by block 320*f*, in some implementations, the pharmaceutical article is a first pharmaceutical drug. In some implementations, a first user type of the respective user types includes a first group of physicians that prescribe the first pharmaceutical drug and a second user type of the respective user types includes a second group of physicians that prescribe a second pharmaceutical drug. In some implementations, the corresponding expected engagement values include a first expected engagement value for the first group of physicians that, based on prescription data, prescribe the first pharmaceutical drug. In some implementations, the corresponding expected engagement values include a second expected engagement value, for the second group of physicians that, based on the prescription data, prescribe the second pharmaceutical drug instead of the first pharmaceutical drug. For example, the expected engagement value for doctors that already prescribe a pharmaceutical drug may be different from (e.g., less than or greater than) the expected engagement value for doctors that currently do not prescribe the pharmaceutical drug. As an example, doctors that prescribe a comparable pharmaceutical drug (e.g., a pharmaceutical drug manufactured by another pharmaceutical manufacturer) may be more interested in viewing information regarding the pharmaceutical drug and prescribing the pharmaceutical drug as an alternative to the comparable pharmaceutical drug that the doctors currently prescribe. In some implementations, determining the respective content templates includes determining, for the first group of physicians, a first content template that includes a first set of data fields for information regarding the first pharmaceutical drug. In some implementations, determining the respective content templates includes determining, for the second group of physicians, a second content template that includes the first set of data fields and a second set of data fields for information comparing the first pharmaceutical drug with the second pharmaceutical drug. For example, the second content template may include a section that the device can populate with information regarding differences between the first pharmaceutical drug and the second pharmaceutical drug. As another example, the second content template may include a section that the device can populate with information that conveys advantages of the first pharmaceutical drug over the second pharmaceutical drug. In some implementations, the second content template includes a section that the device can populate with information regarding prescribing the first pharmaceutical drug via a prescription generation system that the second group of physicians uses (e.g., a pre-populated prescription for the first pharmaceutical drug that the second group of physicians can invoke by entering a brief phrase).

As represented by block 330, in some implementations, the method 300 includes determining, based on the corresponding expected engagement values, respective content templates for the plurality of pharmaceutical content items. For example, as shown in FIG. 1C, the content generator 200 determines the templates 250*a*, 250*c*, 250*e* and 250*f* for the media content items 144, 154, 164 and 174, respectively, based on the expected engagement values 140, 150, 160 and 170, respectively.

As represented by block 330*a*, in some implementations, determining the respective content templates includes selecting, from a plurality of existing content templates, a first content template for a first user type of the respective user types based on a corresponding first expected engagement value of the corresponding expected engagement values. In some implementations, determining the respective content templates includes selecting, from the plurality of existing content templates, a second content template for a second user type of the respective user types based on a corresponding second expected engagement value of the corresponding expected engagement values. For example, as shown in FIG. 2A, the template determiner 230 selects the subset 232 of the templates 250 from the template store 240 based on the expected engagement values 224. As described in relation to FIG. 2A, the template determiner 230 selects the first selected template 232a for the first user type 212a based on the first expected engagement value 224a and the second selected template 232b for the second user type 212b based on the second expected engagement value 224b.

In some implementations, the method 300 includes synthesizing a new template. In some implementations, the method 300 includes synthesizing the new template in response to determining that existing templates are not suitable for a user type based on an expected engagement value associated with the user type. In some implementations, synthesizing the new template includes modifying an existing template. In some implementations, synthesizing the new template includes combining portions of two or more existing templates. In some implementations, synthesizing the new template includes discarding a portion of an existing template.

As represented by block 340, in some implementations, the method 300 includes synthesizing the plurality of pharmaceutical content items by populating the respective content templates with information regarding the pharmaceutical article. For example, as shown in FIG. 1C, the content generator 200 synthesizes the media content items 144, 154, 164 and 174 by populating the templates 250a, 250c, 250e and 250f, respectively, with information stored in the content datastore 280. As another example, as shown in FIG. 2, the template populator 270 generates the media content items 272 by populating the selected templates 232 with information stored in the content datastore 280. In various implementations, synthesizing media content items based on expected engagement values increases a relevance of the media content items to the respective user types. In some implementations, generating media content items that are relevant to specific user types tends to increase engagement with the media content items. In some implementations, increasing engagement with the media content items tends to reduce an amount of time during which a display of a device is unnecessarily kept on thereby enhancing operability of the device by reducing power consumption and extending a battery-life of the device. In some implementations, increasing engagement with the media content items tends to enhance a user experience provided by the device.

As represented by block 340a, in some implementations, synthesizing the plurality of pharmaceutical content items includes synthesizing, for a first user type of the respective user types, a first one of the plurality of pharmaceutical content items by populating a first content template of the respective content templates with a first type of information specified by the first content template. In some implementations, the first type of information includes information that is associated with a first degree of specificity, for example, an advertisement for a pharmaceutical drug. In some implementations, the first type of information includes information that is associated with a first delivery modality, for example, text. For example, as shown in FIG. 2B, the first template 250a may specify that the first template 250a is associated with the first combination of modalities 251a. As such, the device populates the first template 250a with information that is associated with the first combination of modalities 251a. In some implementations, synthesizing the plurality of pharmaceutical content items includes synthesizing, for a second user type of the respective user types, a second one of the plurality of pharmaceutical content items by populating a second content template of the respective content templates with a second type of information specified by the second content template. In some implementations, the second type of information is different from the first type of information. In some implementations, the second type of information includes information that is associated with a second degree of specificity, for example, results of a clinical study for the pharmaceutical drug. In some implementations, the second type of information includes information that is associated with a second delivery modality, for example, video. For example, as shown in FIG. 2B, the second template 250b may specify that the second template 250b is associated with the second combination of modalities 251b. As such, the device populates the second template 250b with information that is associated with the second combination of modalities 251b.

As represented by block 340b, in some implementations, synthesizing the plurality of pharmaceutical content items includes synthesizing, for a first user type of the respective user types, a first one of the plurality of pharmaceutical content items by populating a first number of data fields (e.g., a first number of GUI elements) in a first content template of the respective content templates with information regarding the pharmaceutical article. For example, as shown in FIG. 2B, the first template 250a may include the first set of data fields 252a (e.g., the first set of GUI elements), and the device populates the first template 250a by writing data into the first set of data fields 252a. In some implementations, synthesizing the plurality of pharmaceutical content items includes synthesizing, for a second user type of the respective user types, a second one of the plurality of pharmaceutical content items by populating a second number of data fields (e.g., a second number of GUI elements) in a second content template of the respective content templates with information regarding the pharmaceutical article. In some implementations, the second number is different from the first number. For example, as shown in FIG. 2B, the second template 250b may include the second set of data fields 252b (e.g., the second set of GUI elements), and the device populates the second template 250b by writing data into the second set of data fields 252b.

As represented by block 340c, in some implementations, synthesizing the plurality of pharmaceutical content items includes synthesizing, for a first user type of the respective user types, a first one of the plurality of pharmaceutical content items by populating a first content template of the respective content templates with information associated with a first set of linguistic characteristics specified by the first content template. For example, as shown in FIG. 2B, the first template 250a specifies that the first template 250a is to be populated with information that satisfies the first set of linguistic characteristics 254a. For example, the first template 250a specifies that the first template 250a is to be populated with information that uses objective phrases or sentences. In some implementations, the device uses objective language for a pharmaceutical content item that is tailored for healthcare providers. As described in relation to FIG. 2A, in some implementations, the language synthesizer 276 synthesizes language (e.g., sentences or phrases) that satisfy linguistic characteristics associated with the selected templates 232. For example, if the first template 250a is to be populated with objective language, the language synthesizer 276 selects phrases from a known set of objective phrases. In some implementations, synthesizing the plurality of pharmaceutical content items includes synthesizing, for a second user type of the respective user types, a second one of the plurality of pharmaceutical content items by populating a second content template of the respective content templates with information associated with a second set of linguistic characteristics specified by the second content template. For example, as shown in FIG. 2B, the second template 250b specifies that the second template 250b is to be populated with information that satisfies the second set of linguistic characteristics 254b. For example, the second template 250b specifies that the second template 250b is to be populated with information that uses persuasive phrases or sentences. In the example of populating the second template 250b, the language synthesizer 276 can select phrases from a known set of persuasive phrases. In some implementations, the device uses persuasive language for a pharmaceutical content item that is tailored to patients (e.g., an advertisement for patients).

As represented by block 340d, in some implementations, synthesizing the plurality of pharmaceutical content items includes synthesizing, for a first user type of the respective user types, a first one of the plurality of pharmaceutical content items by populating a first content template of the respective content templates with information that satisfies a first information delivery criterion associated with the first user type. As an example, a template for patients may specify that the template is to be populated with warning labels required by the Food and Drug Administration (FDA). In some implementations, synthesizing the plurality of pharmaceutical content items includes synthesizing, for a second user type of the respective user types, a second one of the plurality of pharmaceutical content items by populating a second content template of the respective content templates with information that satisfies a second information delivery criterion associated with the second user type, where the second information delivery criterion is different from the first information delivery criterion. As an example, a template for physicians may specify that the template is to be populated with clinical information (e.g., as required by the FDA). In some implementations, the information delivery criteria are set by an information validation entity, for example, a regulatory entity such as the FDA.

As represented by block 340e, in some implementations, synthesizing the plurality of pharmaceutical content items includes synthesizing, for a first user type of the respective user types, a first one of the plurality of pharmaceutical content items by retrieving information stored in association with a first set of data fields of a datastore. For example, the template populator 270 (shown in FIG. 2A) can populate the first selected template 232a by retrieving values stored in a first subset of the data fields 282 of the content datastore 280. In some implementations, synthesizing the plurality of pharmaceutical content items includes synthesizing, for a second user type of the respective user types, a second one of the plurality of pharmaceutical content items by retrieving information stored in association with a second set of data fields of the datastore, where the second set is different from the first set. For example, the template populator 270 (shown in FIG. 2A) can populate the second selected template 232b by retrieving values stored in a second subset of the data fields 282 of the content datastore 280. The second subset of the data fields 282 may be different from the first subset of the data fields 282.

As represented by block 340f, in some implementations, synthesizing the plurality of pharmaceutical content items includes synthesizing, for a first user type of the respective user types, a first one of the plurality of pharmaceutical content items by extracting information from a first set of existing pharmaceutical content items. For example, the template populator 270 (shown in FIG. 2A) can populate the first selected template 232a by extracting information from a first subset of the domain-specific media content items 284. In some implementations, synthesizing the plurality of pharmaceutical content items includes synthesizing, for a second user type of the respective user types, a second one of the plurality of pharmaceutical content items by extracting information from a second set of existing pharmaceutical content items. In some implementations, the second set is different from the first set. For example, the template populator 270 (shown in FIG. 2A) can populate the second selected template 232b by extracting information from a second subset of the domain-specific media content items 284, where the second subset may be different from the first subset.

Figure 4:
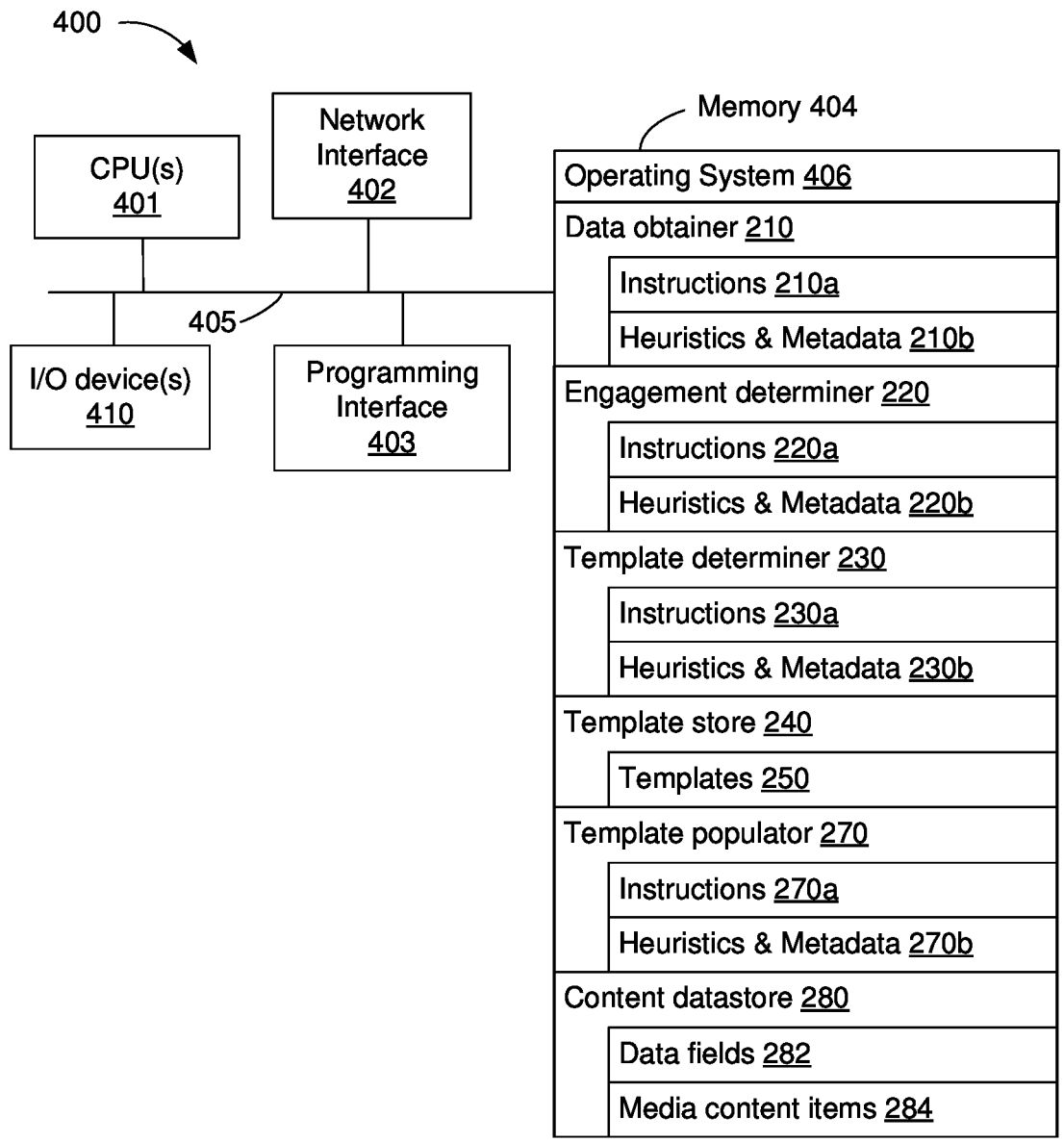
FIG. 4 is a block diagram of a device that generates content for different user types in accordance with some implementations.

FIG. 4 is a block diagram of a device 400 that generates content for different user types in accordance with some implementations. In some implementations, the device 400 implements the device 20 shown in FIGS. 1A-1G, and/or the content generator 200 shown in FIGS. 1A-2. In some implementations, the device 400 is implemented by a server. In some implementations, the device 400 is implemented by a cloud computing platform. While certain specific features are illustrated, those of ordinary skill in the art will appreciate from the present disclosure that various other features have not been illustrated for the sake of brevity, and so as not to obscure more pertinent aspects of the implementations disclosed herein. To that end, as a non-limiting example, in some implementations, the device 400 includes one or more processing units (CPUs) 401, a network interface 402, a programming interface 403, a memory 404, one or more input/output (I/O) devices 410, and one or more communication buses 405 for interconnecting these and various other components.

In some implementations, the network interface 402 is provided to, among other uses, establish and maintain a metadata tunnel between a cloud hosted network management system and at least one private network including one or more compliant devices. In some implementations, the one or more communication buses 405 include circuitry that interconnects and controls communications between system components. The memory 404 includes high-speed random access memory, such as DRAM, SRAM, DDR RAM or other random access solid state memory devices, and may include non-volatile memory, such as one or more magnetic disk storage devices, optical disk storage devices, flash memory devices, or other non-volatile solid state storage devices. The memory 404 optionally includes one or more storage devices remotely located from the one or more CPUs 401. The memory 404 comprises a non-transitory computer readable storage medium.

In some implementations, the memory 404 or the non-transitory computer readable storage medium of the memory 404 stores the following programs, modules and data structures, or a subset thereof including an optional operating system 406, the data obtainer 210, the engagement determiner 220, the template determiner 230, the template store 240, the template populator 270 and the content datastore 280. In various implementations, the device 400 performs the method 300 shown in FIG. 3. In some implementations, the data obtainer 210 includes instructions 210a, and heuristics and metadata 210b for obtaining a request to synthesize media content items for various user types. In some implementations, the engagement determiner 220 includes instructions 220a, and heuristics and metadata 220b for determining corresponding expected engagement values for the user types. In some implementations, the template determiner 230 includes instructions 230a, and heuristics and metadata 230b for determining respective templates for the user types based on their corresponding expected engagement values. In some implementations, the template populator 270 includes instructions 270a, and heuristics and metadata 270b for populating the templates determined by the template determiner 230 with information stored in the content datastore 280.

In various implementations, the one or more I/O devices 410 include one or more sensors. In some implementations, the one or more I/O devices 410 include a receiver for receiving the request to synthesize media content items for various user types. In some implementations, the one or more I/O devices 410 include a transmitter for transmitting the media content items after the device 400 has synthesized the media content items. In some implementations, the one or more I/O devices 410 include a display for displaying a GUI (e.g., the content generation GUI 30 shown in FIGS. 1A and 1B, and/or the content presentation GUI 130 shown in FIGS. 1C-1E). In some implementations, the one or more I/O devices 410 include a speaker for outputting audible signals corresponding to the synthesized media content items. In some implementations, the one or more I/O devices 410 include a haptic device (e.g., a vibration device, for example, a motor with an unbalanced load or a piezoelectric device) for outputting haptic responses corresponding to the synthesized media content items.

While various aspects of implementations within the scope of the appended claims are described above, it should be apparent that the various features of implementations described above may be embodied in a wide variety of forms and that any specific structure and/or function described above is merely illustrative. Based on the present disclosure one skilled in the art should appreciate that an aspect described herein may be implemented independently of any other aspects and that two or more of these aspects may be combined in various ways. For example, an apparatus may be implemented and/or a method may be practiced using any number of the aspects set forth herein. In addition, such an apparatus may be implemented and/or such a method may be practiced using other structure and/or functionality in addition to or other than one or more of the aspects set forth herein.

It will also be understood that, although the terms "first", "second", etc. may be used herein to describe various elements, these elements should not be limited by these terms. These terms are only used to distinguish one element from another. For example, a first node could be termed a second node, and, similarly, a second node could be termed a first node, which changing the meaning of the description, so long as all occurrences of the "first node" are renamed consistently and all occurrences of the "second node" are renamed consistently. The first node and the second node are both nodes, but they are not the same node.

The terminology used herein is for the purpose of describing particular implementations only and is not intended to be limiting of the claims. As used in the description of the implementations and the appended claims, the singular forms "a", "an", and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting", that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

What is claimed is:

1. A method comprising:
    at a device including a display, a non-transitory memory and a processor coupled with the display and the non-transitory memory:
        displaying, on the display, a graphical user interface (GUI) to synthesize a plurality of pharmaceutical content items for respective user types, wherein the plurality of pharmaceutical content items provides information regarding a pharmaceutical article, wherein the GUI includes:
            a first selectable user interface (UI) element for selecting a first user type from the respective user types;
            a second selectable UI element for selecting a second user type from the respective user types;
            a third selectable UI element for selecting a third user type from the respective user types; and
            a button for triggering generation of the plurality of pharmaceutical content items after two or more of the first, second and third selectable UI elements have been selected;
        detecting user inputs selecting the first selectable UI element and the second selectable UI element;
        determining a first content template for the first user type and a second content template for the second user type; and
        synthesizing the plurality of pharmaceutical content items by populating the first and second content templates with information regarding the pharmaceutical article.

2. The method of claim 1, wherein the first selectable UI element includes a first check box, the second selectable UI element includes a second check box and the third selectable UI element includes a third check box.

3. The method of claim 1, wherein the GUI further includes:
    a first controllable UI element that is displayed adjacent to the first selectable UI element and the first controllable UI element accepts a first expected engagement value that is utilized to determine the first content template for the first user type; and a second controllable UI element that is displayed adjacent to the second selectable UI element and the second controllable UI element accepts a second expected engagement value that is utilized to determine the second content template for the second user type.

4. The method of claim 1, wherein the GUI further includes:
a first controllable UI element that is displayed adjacent to the first selectable UI element and the first controllable UI element accepts a first time duration value that is utilized to determine the first content template for the first user type; and
a second controllable UI element that is displayed adjacent to the second selectable UI element and the second controllable UI element accepts a second time duration value that is utilized to determine the second content template for the second user type.

5. The method of claim 1, wherein the GUI further includes:
a first controllable UI element that is displayed adjacent to the first selectable UI element and the first controllable UI element accepts a first content size value that is utilized to determine the first content template for the first user type; and
a second controllable UI element that is displayed adjacent to the second selectable UI element and the second controllable UI element accepts a second content size value that is utilized to determine the second content template for the second user type.

6. The method of claim 1, wherein the GUI further includes:
a first controllable UI element that is displayed adjacent to the first selectable UI element and the first controllable UI element accepts a first user comprehension value that is utilized to determine the first content template for the first user type; and
a second controllable UI element that is displayed adjacent to the second selectable UI element and the second controllable UI element accepts a second user comprehension value that is utilized to determine the second content template for the second user type.

7. The method of claim 1, wherein the plurality of pharmaceutical content items includes a first pharmaceutical content item for the first user type, and the method further comprises:
concurrently displaying a representation of the first pharmaceutical content item and a modify UI element to modify the first pharmaceutical content item;
in response to detecting a user input directed to the modify UI element, modifying the first pharmaceutical content item by switching from the first content template to a third content template.

8. A non-transitory memory storing one or more programs, which, when executed by one or more processors of a device with a display, cause the device to:
display, on the display, a graphical user interface (GUI) to synthesize a plurality of pharmaceutical content items for respective user types, wherein the plurality of pharmaceutical content items provides information regarding a pharmaceutical article, wherein the GUI includes:
a first selectable user interface (UI) element for selecting a first user type from the respective user types;
a second selectable UI element for selecting a second user type from the respective user types;
a third selectable UI element for selecting a third user type from the respective user types; and
a button for triggering generation of the plurality of pharmaceutical content items after two or more of the first, second and third selectable UI elements have been selected;
detect user inputs selecting the first selectable UI element and the second selectable UI element;
determine a first content template for the first user type and a second content template for the second user type; and
synthesize the plurality of pharmaceutical content items by populating the first and second content templates with information regarding the pharmaceutical article.

9. The non-transitory memory of claim 8, wherein the first selectable UI element includes a first check box, the second selectable UI element includes a second check box and the third selectable UI element includes a third check box.

10. The non-transitory memory of claim 8, wherein the GUI further includes:
a first slidable UI element that is displayed adjacent to the first selectable UI element and the first slidable UI element accepts a first expected engagement value that is utilized to select the first content template for the first user type; and
a second slidable UI element that is displayed adjacent to the second selectable UI element and the second slidable UI element accepts a second expected engagement value that is utilized to select the second content template for the second user type.

11. The non-transitory memory of claim 8, wherein the GUI further includes:
a first drop-down UI element that is displayed adjacent to the first selectable UI element and the first drop-down UI element accepts selection of a first time duration value that is utilized to select the first content template for the first user type; and
a second drop-down UI element that is displayed adjacent to the second selectable UI element and the second drop-down UI element accepts selection of a second time duration value that is utilized to select the second content template for the second user type.

12. The non-transitory memory of claim 8, wherein the GUI further includes:
a first controllable UI element that is displayed adjacent to the first selectable UI element and the first controllable UI element accepts a first content size value that is utilized to select the first content template for the first user type; and
a second controllable UI element that is displayed adjacent to the second selectable UI element and the second controllable UI element accepts a second content size value that is utilized to select the second content template for the second user type.

13. The non-transitory memory of claim 8, wherein the GUI further includes:
a first controllable UI element that is displayed adjacent to the first selectable UI element and the first controllable UI element accepts a first user comprehension value that is utilized to select the first content template for the first user type; and
a second controllable UI element that is displayed adjacent to the second selectable UI element and the second controllable UI element accepts a second user comprehension value that is utilized to select the second content template for the second user type.

14. The non-transitory memory of claim 8, wherein the plurality of pharmaceutical content items includes a first pharmaceutical content item for the first user type, and the one or more programs further cause the device to:
- concurrently display a representation of the first pharmaceutical content item and a modify UI element to modify the first pharmaceutical content item; and
- in response to detecting a user input directed to the modify UI element, modify the first pharmaceutical content item by switching from the first content template to a third content template.

15. A device comprising:
- a display;
- one or more processors;
- a non-transitory memory; and
- one or more programs stored in the non-transitory memory, which, when executed by the one or more processors, cause the device to:
  - display, on the display, a graphical user interface (GUI) to synthesize a plurality of pharmaceutical content items for respective user types, wherein the plurality of pharmaceutical content items provides information regarding a pharmaceutical article, wherein the GUI includes:
    - a first selectable user interface (UI) element for selecting a first user type from the respective user types;
    - a second selectable UI element for selecting a second user type from the respective user types;
    - a third selectable UI element for selecting a third user type from the respective user types; and
    - a button for triggering generation of the plurality of pharmaceutical content items after two or more of the first, second and third selectable UI elements have been selected;
  - detect user inputs selecting the first selectable UI element and the second selectable UI element;
  - determine a first content template for the first user type and a second content template for the second user type; and
  - synthesize the plurality of pharmaceutical content items by populating the respective first and second content templates with information regarding the pharmaceutical article.

16. The device of claim 15, wherein the first selectable UI element includes a first check box, the second selectable UI element includes a second check box and the third selectable UI element includes a third check box.

17. The device of claim 15, wherein the GUI further includes:
- a first slidable UI element that is displayed adjacent to the first selectable UI element and the first slidable UI element is for selecting a first expected engagement value that is utilized to select the first content template for the first user type; and
- a second slidable UI element that is displayed adjacent to the second selectable UI element and the second slidable UI element is for selecting a second expected engagement value that is utilized to select the second content template for the second user type.

18. The device of claim 15, wherein the GUI further includes:
- a first drop-down UI element that is displayed adjacent to the first selectable UI element and the first drop-down UI element is for receiving a first time duration value that is utilized to select the first content template for the first user type; and
- a second drop-down UI element that is displayed adjacent to the second selectable UI element and the second drop-down UI element is for receiving a second time duration value that is utilized to select the second content template for the second user type.

19. The device of claim 15, wherein the GUI further includes:
- a first controllable UI element that is displayed adjacent to the first selectable UI element and the first controllable UI element accepts a first content size value that is utilized to select the first content template for the first user type; and
- a second controllable UI element that is displayed adjacent to the second selectable UI element and the second controllable UI element accepts a second content size value that is utilized to select the second content template for the second user type.

20. The device of claim 15, wherein the plurality of pharmaceutical content items includes a first pharmaceutical content item for the first user type, and the one or more programs further cause the device to:
- concurrently display a representation of the first pharmaceutical content item and a modify UI element to modify the first pharmaceutical content item; and
- in response to detecting a user input directed to the modify UI element, modify the first pharmaceutical content item by switching from the first content template to a third content template.

* * * * *